(12) United States Patent
Sanchez et al.

(10) Patent No.: US 6,743,225 B2
(45) Date of Patent: Jun. 1, 2004

(54) ELECTROPHYSIOLOGIC MEASURE OF ENDPOINTS FOR ABLATION LESIONS CREATED IN FIBRILLATING SUBSTRATES

(75) Inventors: Javier E. Sanchez, Homewood, AL (US); Jeffrey A. Hall, Birmingham, AL (US); Michael E. Benser, Birmingham, AL (US); Raymond E. Ideker, Birmingham, AL (US); William M. Smith, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 501 days.

(21) Appl. No.: 09/818,206

(22) Filed: Mar. 27, 2001

(65) Prior Publication Data

US 2003/0028183 A1 Feb. 6, 2003

(51) Int. Cl.$^7$ ............................................. A61B 18/04

(52) U.S. Cl. ........................ 606/34; 607/101; 607/105; 606/32; 606/41; 606/51; 128/898

(58) Field of Search ............................ 606/32, 34, 35, 606/39, 40, 41, 42, 46, 47, 48, 49, 50, 51, 52, 213; 607/96, 98, 99, 100, 101, 113, 115, 116, 114, 105; 128/898

(56) References Cited

U.S. PATENT DOCUMENTS

| | | | |
|---|---|---|---|
| 5,364,352 A | 11/1994 | Cimino et al. ............... 604/95 |
| 5,452,733 A | * 9/1995 | Sterman et al. ............ 128/898 |
| 5,492,119 A | 2/1996 | Abrams ...................... 128/642 |
| 5,571,215 A | * 11/1996 | Sterman et al. ............ 128/898 |
| 5,596,995 A | 1/1997 | Sherman et al. ............ 128/736 |
| 5,606,974 A | 3/1997 | Castellano et al. ..... 128/662.06 |
| 5,617,854 A | 4/1997 | Munsif ...................... 128/642 |
| 5,662,606 A | 9/1997 | Cimino et al. ............... 604/95 |
| 5,666,970 A | 9/1997 | Smith ......................... 128/772 |
| 5,681,280 A | 10/1997 | Rusk et al. .................. 604/95 |
| 5,735,280 A | 4/1998 | Sherman et al. ........ 128/600.03 |

(List continued on next page.)

OTHER PUBLICATIONS

Avitall et al., "The Creation of Linear Contiguous Lesions in the Atria With an Expandable Loop Catheter," J. Am. College of Cardio., 33(4):972–984 (Mar. 15, 1999).
Calkins et al., "A New System for Catheter Ablation of Atrial Fibrillation," Am. J. of Cardio., 83(5B):227D–236D (Mar. 11, 1999).
Gepstein et al., "Atrial Linear Ablations in Pigs Chronic Effects on Atrial Electrophysiology and Pathology," Circulation, 419–426 (Jul. 27, 1999).
Liem et al., "Electrophysiological Correlates of Transmural Linear Ablation," PACE, 23:40–46 (1/2000).
Nakagawa et al., "Use of Atrial Potential Attenuation to Identify Endpoint of Radiofrequency Application for Continuous, Transmural Linear Atrial Ablation," Circulation (Abstract) 96:I–451 (1997).
Taylor et al., "High–Resolution Mapping and Histologic Examination of Long Radiofrequency Lesions in Canine Atria," J. Cardiovasc. Electrophysiol., 10(11):1467–1477 (11/99).
PCT International Search Report, International Application No. PCT/US02/09388 dated Dec. 19, 2002.

*Primary Examiner*—Henry Bennett
*Assistant Examiner*—Fadi H. Dahbour
(74) *Attorney, Agent, or Firm*—Myers Bigel Sibley & Sajovec PA

(57) ABSTRACT

Methods, systems, and computer program products measure electrical activity of the cardiac tissue proximate the lesion site during an ablation treatment, and then compare the measurements to determine whether the lesion is clinically efficacious so as to be able to block myocardial propagation. The methods can include obtaining the measurements and performing the ablation therapy while the subject is experiencing atrial fibrillation and may measure the standard deviation of the electrogram signal.

44 Claims, 16 Drawing Sheets

U.S. PATENT DOCUMENTS

| | | | |
|---|---|---|---|
| 5,741,320 A | 4/1998 | Thornton et al. | 607/122 |
| 5,797,960 A * | 8/1998 | Stevens et al. | 606/213 |
| 5,810,740 A | 9/1998 | Paisner | 600/515 |
| 5,857,997 A | 1/1999 | Cimino et al. | 604/95 |
| 5,954,665 A | 9/1999 | Ben-Haim | 600/515 |
| 5,971,980 A | 10/1999 | Sherman | 606/34 |
| 6,042,580 A | 3/2000 | Simpson | 606/32 |
| 6,045,550 A | 4/2000 | Simpson et al. | 606/42 |
| 6,049,737 A | 4/2000 | Simpson et al. | 607/119 |
| 6,050,994 A | 4/2000 | Sherman | 606/42 |
| 6,059,778 A | 5/2000 | Sherman | 606/34 |
| 6,071,281 A * | 6/2000 | Burnside et al. | 606/41 |
| 6,099,524 A | 8/2000 | Lipson et al. | 606/41 |
| 6,113,592 A | 9/2000 | Taylor | 606/34 |
| 6,146,381 A | 11/2000 | Bowe et al. | 606/41 |
| 6,161,543 A * | 12/2000 | Cox et al. | 128/898 |
| 6,546,935 B2 * | 4/2003 | Hooven | 128/898 |

* cited by examiner

ELECTROPHYSIOLOGIC MEASURE OF ENDPOINTS FOR ABLATION LESIONS CREATED IN FIBRILLATING SUBSTRATES

FIELD OF THE INVENTION

The present invention is related to cardiac ablation treatments.

BACKGROUND OF THE INVENTION

Ablation therapies can be used to treat certain conditions of the heart including atrial fibrillation. Ablation therapies are typically administered to regions in the heart to kill tissue and form lesions in selected heart tissue such that the lesion formed by the ablated heart tissue is unable to support conduction, and hence, fibrillation.

Generally stated, during atrial fibrillation, propagation of the electrical excitation wavefront travels along the surface substrate tissue (wall). To be effective, the ablated tissue lesion should be transmural such that the tissue is destroyed along the surface and through the thickness of the substrate tissue (or the thickness of the wall) about the lesion (i.e., not merely a surface or superficial lesion). Typically, the ablation therapy is delivered so that a desired contiguous (conventionally linear) lesion pattern or length is formed in the selected myocardial tissue, which kills all viable excitable cells about the surface of the lesion and through the wall thickness underlying the lesion so that the heart is unable to maintain fibrillation. That is, the lesion electrically insulates and separates side-by-side adjacent segments in the atria so that the adjacent segments are effectively electrically isolated from each other by the lesion in a manner that inhibits electrical conduction between the adjacent segments.

In some applications, transvenous or intravenous ablation catheters having one or more electrodes can be inserted into one or more heart cavities to administer the ablation treatment to kill selected heart tissue. Unfortunately, in conventional ablation treatments, it can be difficult to assess when to terminate the administration of the treatment in a manner which identifies when sufficient tissue has been destroyed to provide a clinically efficacious (transmural) linear ablation lesion. Particularly, "blind" or catheter-based ablation of cardiac tissue (such as to treat atrial fibrillation) may be more effective when patient-specific valid endpoints are used to recognize when a clinically efficacious lesion has been created. In the early ablation experience, acute termination followed by non-inducibility of the arrhythmia were used. Because these endpoints correlated poorly with long-term success, however, other parameters were developed. Presently, it is believed that impedance and temperature measurements during the delivery of RF energy and the presence of conduction block after delivery of RF energy are the most common endpoints used in clinical practice.

SUMMARY OF THE INVENTION

The present invention provides methods, systems, and computer program products for assessing the condition of the lesion formed in cardiac tissue during myocardial ablation. The systems and methods and computer programs of the invention can be used to monitor the lesion site and identify when sufficient necrosis has occurred. Further, in certain embodiments, the administration of the selected cardiac ablation therapy can be controlled so as to automatically terminate the ablation treatment upon the determination that the lesion site is a clinically efficacious lesion during an ablation procedure. The term "clinically efficacious" is meant to indicate that the lesion is able to substantially block myocardial propagation between adjacent tissue segments and, as such, includes the term "transmural" which means that the extent of necrosis is such that the substrate or tissue destroyed by the ablation procedure to create the lesion is contiguous about the surface of the lesion site and extends through the thickness of the wall to electrically isolate adjacent segments positioned on opposing sides of the lesion. The transmural nature of the lesiton site is also indicated when myocardial necrosis is sufficient to extend from the endocardial to the epicardial layer.

In certain embodiments, the methods and systems of the present invention can be used while a subject is experiencing fibrillation (typically atrial fibrillation). In other embodiments, the systems and methods can be used during normal sinus rhythm.

Certain embodiments of the present invention are directed to methods for controlling the administration of an ablation treatment to cardiac tissue of a patient experiencing (an onset of or a continued state of unstable or fibrillating state). The method can include the steps of: (a) measuring at least one electrophysiologic parameter of heart tissue proximate a targeted ablation treatment region while the patient is in atrial fibrillation; (b) ablating the targeted ablation treatment region to form a lesion in cardiac tissue; (c) measuring the at least one electrophysiologic parameter of cardiac tissue proximate the targeted ablation treatment region after the first measuring step and after the ablating step has been commenced while the patient is in atrial fibrillation; (d) comparing the at least one electrophysiologic parameter measured during steps (a) and (c) to determine whether the lesion formed by the ablating step is clinically efficacious.

In certain embodiments, methods for controlling the delivery of a selected ablation treatment to cardiac tissue can include the steps of: delivering a desired ablation therapy to the selected ablation treatment region to form a lesion in the cardiac tissue; obtaining first and second measurements of at least one electrophysiologic signal associated with cardiac tissue in the selected ablation treatment region from a plurality of different positions associated with the lesion, wherein the first measurements are obtained before the delivering step is initiated; and comparing the first and second measurements of the obtaining step to identify when sufficient tissue has been destroyed at the lesion so as to stop the ablation of the tissue of the delivering step.

In certain embodiments, the delivering step may be carried out by a multiple electrode RF ablation catheter, and the obtaining step can include sensing the electrical activity of the at least one electrophysiologic signal from a plurality of different electrical couplings of the multiple electrodes on the ablation catheter.

Still other embodiments are directed to methods for identifying when a lesion is clinically efficacious during delivery of a selected ablation therapy to form same. The methods can include: (a) measuring the standard deviation of electrogram amplitude of heart tissue proximate a targeted ablation treatment region while the patient is in atrial fibrillation; (b) ablating the targeted ablation treatment region to form a lesion in the heart tissue; (c) measuring the standard deviation of the electrogram amplitude of heart tissue proximate the targeted ablation treatment region after the first measuring step and after the ablating step has been commenced (during ablation or as the ablation is temporally halted) while the patient is in atrial fibrillation; (d) comparing the standard deviation measure of the electrogram amplitude measured during steps (a) and (c); and (e) determining whether the lesion formed by the ablating step is clinically efficacious based on the comparing step.

In some embodiments, the method can also include the step of measuring the ablation treatment temperature and time during the ablating step, and the determining step can further consider the temperature and time to assess whether the lesion is clinically efficacious (or transmural).

In certain embodiments, systems for ablating cardiac tissue can include an ablation source configured to expose targeted cardiac tissue to temperatures above about 45° C. for a period of time to form a lesion in cardiac tissue. The system can also include a controller operably associated with the ablation source and a power source operably associated with the controller and the ablation source. The system can include a plurality of (sensing) electrodes operably associated with the controller and configured to be positioned, in operation, proximate the lesion site of the targeted cardiac tissue. In operation, the controller receives electrical signals corresponding to electrical activity of the cardiac tissue about the lesion from the electrodes before initiation of the thermal ablation therapy and at desired times during the ablation therapy treatment session. The controller analyzes the electrical signals to control the duration of the ablation treatment from the ablation source. The electrodes are configured to relay information to the controller about the electrical activity of the cardiac tissue about the lesion and to ablate the tissue at the lesion site.

In certain embodiments, the ablation source comprises a multiple electrode catheter configured to transmit RF energy to the cardiac tissue and the multiple electrodes can be configured such that, in operation, they can be electrically switched so as to be coupled in a plurality of different manners to sense and relay information to the controller about electrical activity over larger regions about the lesion.

In other embodiments, systems for ablating cardiac tissue can include an ablation source configured to expose targeted cardiac tissue to temperatures above about 45° C. for a period of time to form a lesion in cardiac tissue and a controller operably associated with the ablation source. The system can also include a power source operably associated with the controller and the ablation source and at least one sensing electrode operably associated with the controller and configured, in operation, to be positioned proximate the lesion site of the targeted cardiac tissue. The controller is configured to receive electrical signals from the at least one sensing electrode before initiation of the thermal ablation therapy and at desired times during the ablation therapy treatment session. The electrical signals can be obtained during (atrial) fibrillation and can correspond to the measure of the standard deviation of the electrogram amplitude of the tissue during fibrillation. The controller (or computer programs or data processing systems associated therewith) is configured to analyze the standard deviation of the amplitude of the fibrillating tissue about the lesion to control the duration of the ablation treatment from the ablation source.

Other embodiments include computer program products for identifying whether an ablation lesion in cardiac tissue of a subject being treated for a cardiac condition is clinically efficacious during an ablation therapy session. The computer program product can include a computer readable storage medium having computer readable program code embodied in the medium. The computer-readable program code can include: (a) computer readable program code for identifying a first measurement of the electrical activity corresponding to the standard deviation of the amplitude of the electrogram in the cardiac tissue located about a lesion site while a subject is experiencing atrial fibrillation; (b) computer readable program code for identifying a second measurement of the electrical activity corresponding to the standard deviation of the amplitude of the electrogram in the cardiac tissue located about the lesion site after the lesion site has been exposed to at least a portion of a selected ablation therapy; and (c) computer readable program code for comparing the first and second measurements of the standard deviation of the amplitude of the electrogram activity to determine whether the lesion is clinically efficacious.

In certain embodiments the computer program product can include computer readable program code for assessing the amount of time, the ablation temperature, and the type of ablation therapy which the tissue proximate the lesion has been exposed and for considering this information in determining the efficacy of the treatment.

Another embodiment of the present invention, similar to the above, is directed to a computer program product for identifying whether an ablation lesion in cardiac tissue of a subject being treated for a cardiac condition is clinically efficacious during an ablation therapy session. The computer program product includes a computer readable storage medium having computer readable program code embodied in said medium. The computer-readable program code can include: (a) computer readable program code for receiving data corresponding to a first set of information regarding the electrical activity in the cardiac tissue from multiple regions about a lesion site prior to active initiation of the ablation therapy; (b) computer readable program code for receiving data corresponding to a second set of information regarding the electrical activity in the cardiac tissue from multiple regions about the lesion site after the lesion site has been exposed to at least a portion of a selected ablation therapy; and (c) computer readable program code for comparing the data from the first and second sets of information to determine whether the lesion is clinically efficacious about its perimeter.

In certain embodiments, the computer program product can include computer readable program code for acquiring and analyzing or "scanning" the lesion site to obtain a plurality of data sets over different spatial regions about the lesion site during the ablation therapy and computer readable program code for electrically changing the couplings of electrodes used to deliver the ablation therapy to electrical sense and relay information about the electrical activity of the lesion site from a plurality of different spatial perspectives during the ablation therapy session.

The foregoing and other objects and aspects of the present invention are explained in detail in the specification set forth below.

DESCRIPTION OF EMBODIMENTS OF THE INVENTION

The present invention will now be described more fully hereinafter with reference to the accompanying figures, in which certain embodiments of the invention are shown. This invention may, however, be embodied in many different forms and should not be construed as limited to the embodiments set forth herein. Like numbers refer to like elements throughout. In the figures, layers, components, features or regions may be exaggerated for clarity. In the block diagrams, the broken line boxes and corresponding lead lines represent optional or alternative applications, method or program steps.

The present invention may be used with systems, methods, and devices configured to ablate the heart for treating (including inhibiting, preventing or halting) cardiac dysfunctions or impairments including forms of cardiac tachyarrhythmias in subjects, including atrial flutter and/or atrial fibrillation. The present invention may be particularly suitable for assessing the clinical efficacy of a lesion formed in cardiac tissue in vivo during an ablation treatment session when the subject is in atrial fibrillation. That is, the subject may be in atrial fibrillation temporally proximate to (before and/or during) the ablation treatment. The lesion, which may be linear, can treat the atrial fibrillation condition by inhibiting or preventing myocardial propagation between adjacent segments of the cardiac tissue disposed on opposing sides of the lesion.

Certain embodiments of the present invention may be able to more reliably indicate when sufficient ablation has been performed during the ablation procedure so as to provide sufficient necrosis to block myocardial propagation through the lesion within this volume, which can provide a reliable indicator that the treatment can be terminated. This may limit the delivery time to that actually necessary for the electrical isolation desired and yet inhibit over-ablating (i.e., continuing to ablate after the lesion is transmural) the cardiac tissue.

Subjects, according to the present invention, can be any animal subject, are preferably mammalian subjects (e.g., humans, canines, felines, bovines, caprines, ovines, equines, rodents, porcines, and/or lagomorphs), and more preferably are human subjects.

Figure 1:
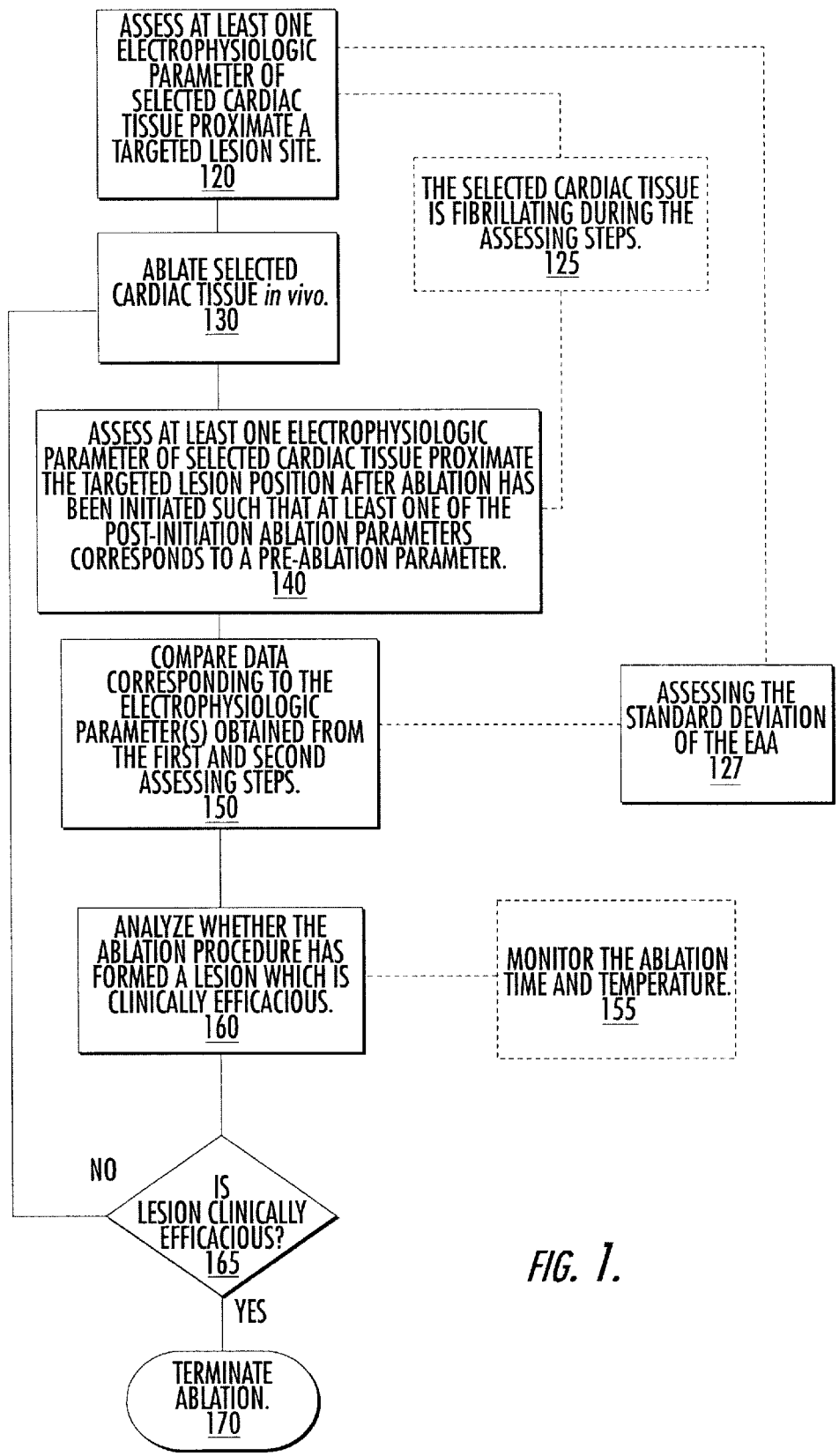
FIG. 1 is a block diagram of a method for controlling the delivery of an ablation therapy to a subject according to embodiments of the present invention.

FIG. 1 illustrates a method according to certain embodiments of the invention. As shown, at least one electrophysiologic parameter of selected cardiac tissue proximate a targeted ablation-imparted lesion site is assessed (Block 120). The electrophysiologic parameter can be a number of suitable parameters representative of the electrical activity of the cardiac tissue corresponding to the lesion site. The electrical activity can include, but is not limited to, electrical signals corresponding to the local electrogram signal (which can include, but is not limited to, the electrogram activation amplitude (EAA)), pacing threshold value, and the like.

For parameters associated with the electrogram signal, various numerical ways to monitor the electrical activity or corresponding detected signals may be used, including, but not limited to, the mean, average, or standard deviation value of the amplitude of the signal(s), the maxima or minima of the amplitude of the signal(s), the slope of a portion of the waveform associated with the signal(s), the peak—peak difference in the signal(s), the mean slew rate of the signal(s), the maximum slew rate of the signal(s), the root mean square power within different frequency bands of the signal(s), the upper and lower frequency band-pass corners of the signal(s), and the flatness of the band-pass of the signal(s).

In other embodiments, the values of a plurality of these parameters are analyzed or combined to increase sensitivity and/or specificity for predicting the clinical efficacy of an ablated tissue region (and or the extent of necrosis of the ablated tissue). In still other embodiments, one or more of the desired electrophysiologic parameters may be combined with other, potentially non-physiologic parameters or measurements as well. Suitable non-physiologic parameters include, but are not limited to, impedance data measurements (such as those relayed from transmitting electrodes), the total, integrated or average power delivered during the ablation, the elapsed duration time of exposure to ablation temperatures, the ablation temperate employed, or the type of ablation source employed. For example, the decrease in standard deviation of the amplitude of the fibrillation electrogram(s) may be combined (computationally) with the ablation time and temperature or type of ablation source and power delivered or impedance measured to define when to terminate the ablation delivery treatment session.

The electrical signal(s) can be obtained over a predetermined time to account for temporal deviation in signal data, such as 1–120 seconds. In certain embodiments, the time interval is about 5–20 seconds, and is typically at least about 10 seconds. In addition, particularly for NSR modes, an actual value of the amplitude at discrete serially consecutive points or desired points in time can be detected and analyzed (e.g., every second).

Electrogram measurements, signals, or readings can be obtained in a number of ways, including unipolar, bipolar, or in combinations of different electrode bands and grounds on multi-pole catheters; the combinations will be discussed further below. In certain embodiments, to account for temporal variability of fibrillatory activation from relatively local electrograms, a recording or sensing duration or period of at least about 10 seconds may be desirable, although other recording durations may be used (or even changed or adjusted during the procedure as desired).

In certain embodiments, the ablation treatment can be administered to a patient which is in atrial fibrillation (Block 125). The AF state can be a natural state or may be an induced fibrillation state, such as induction via an application of an electrical signal or pulse or a chemical or drug. In these embodiments, the present invention can measure one or more parameters of the electrical activity in the AF tissue proximate the tissue site. In some embodiments, the standard deviation of the electrogram amplitude before and the standard deviation of the electrogram signal (Block 127) during or after an applied ablation treatment can be assessed to determine whether the lesion is clinically efficacious.

In certain embodiments, the pre-ablation measurement can be obtained prior to the actual treatment session at a point in time which is separate from the initiation of the ablation therapy. In certain embodiments, the pre-ablation measurement can be based on a statistical norm, conventional signal values, or other predetermined value (i.e., the pre-ablation value can be pre-defined and does not need to be measured individually in each patient).

Alternatively, in other embodiments, there is no need to use a pre-ablation measurement of value as the measurement(s) obtained during the ablation treatment (while the ablation therapy is being actively administered or temporarily halted for measurement) may be sufficient to indicate that the lesion is transmural or clinically efficacious. For example, a measure of the electrogram signal may be such that it has an amplitude which is sufficiently small to represent that the localized tissue is unable to support the propagation of electrical activity about the lesion. Calculation of the standard deviation of the EAA is well known and corresponds to the amplitude of fibrillation. The relationship can be described by the mathematical equation stated below:

$$\frac{\sum_{i=1}^{n}[(y_i - \overline{y})^2]}{n-1}$$

where "y" is a signal, expressed as a discrete function of time "y(t)", and "$\overline{y}$" is the mean of the signal over the range sampled, "n" is the number of sampled points of the signal and $y_i$ is each point of the signal.

Referring again to FIG. 1, the selected cardiac tissue is ablated in vivo (Block 130). To successfully ablate the tissue, it is exposed to temperatures above about 45° C. for a period of time (typically ranging from seconds to minutes, depending on the ablation technology type employed). Typically, the thermal ablation temperature is at least about 50° C. Then, subsequent to initiation of the cardiac ablation therapy, at least one electrophysiologic parameter of selected cardiac tissue proximate the targeted lesion site is assessed (Block 140). The at least one electrophysiologic parameter measured after initiation of the ablation therapy can correspond to the at least one electrophysiologic parameter measured before initiation of the ablation therapy (Block 140). The pre and post-initiation parameters can be compared (Block 150). The values of the pre and post-initiation parameters can be used to analyze whether the ablation procedure has formed a lesion which is clinically efficacious (Block 160) such as impedance and/or delivered power. The comparison can analyze the "before" and "after" signal data (or just the "during" or "after" data as discussed above) to ascertain whether a sufficient reduction in electrical activity has been realized in tissue about the lesion site.

In addition, in certain embodiments, other relevant parameters can be obtained and considered with the reduction in electrical activity measurement analysis. For example, the ablation time and temperature can also be considered during the analyzing step to provide additional information about the condition of the lesion site (Block 155). This ablation time and temperature may be correlated to the type of ablation therapy employed. For example, for an ablation source using RF ablation energy delivered via intracaval catheters at about 50° C., an elapsed duration of thermal exposure at this temperature of about 240 seconds along with a certain reduction in electrical activity can be used to identify when the lesion is clinically efficacious. It is anticipated that an automated analysis such as implemented by a computer program or algorithm may be employed (such as via a look-up chart or statistical or mathematical calculation of received data to pre-determined threshold or ceiling limits or values of relevant parameters) to correlate different temperatures or ablation sources to define different minimum (or maximum) treatment times for different ablation exposure temperatures. Thus, these embodiments can monitor and determine when both (a) the desired thermal exposure time or other desired parameter has been reached (such as power/impedance) and (b) the desired reduction in electrical activity has occurred to define when the lesion can be identified as clinically efficacious.

In any event, based on the analyzed information, the methods, systems, and computer program products of the instant invention can determine whether the lesion is clinically efficacious (Block 165). If so, the ablation therapy is terminated (Block 170). If not, the ablation therapy is continued (Block 130) or re-applied or recommenced and Blocks 140, 150, 160, and 165 can be repeated.

The comparison step can analyze the relative or absolute reduction in the electrical activity. The reduction desired may be different depending on where the lesion site is located (i.e., for the atria, an 80% reduction may correspond to clinical efficacious lesion, whereas for lesions formed in the ventricle, a different reduction value may be used to identify clinical efficacy) or the type of ablation source/power and/or the configuration of the ablation system employed. Larger reduction (in either absolute or relative measures) may be indicative of a larger extent of myocardial necrosis. It is anticipated that clinical studies will allow correlation of the appropriate reduction (relative or absolute) values for the desired lesion site.

Figure 3:
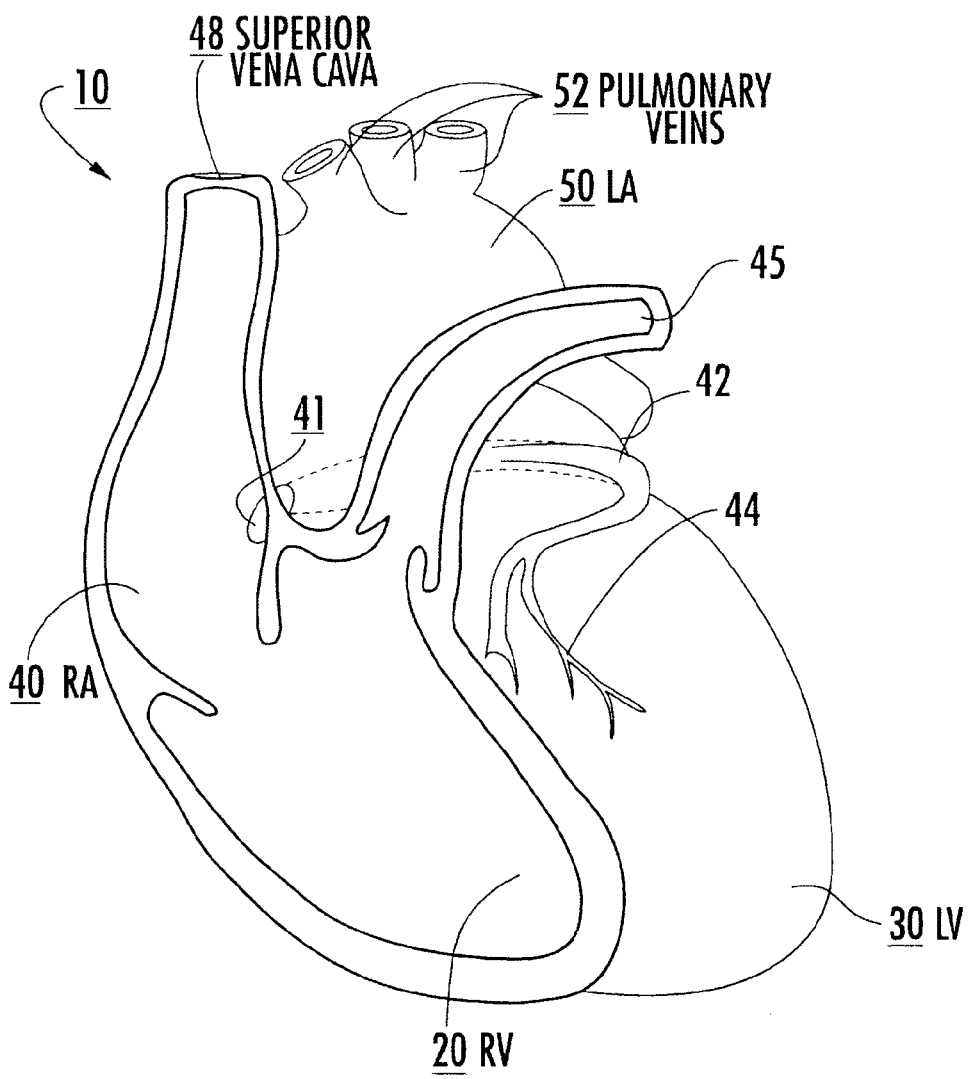
FIG. 3 is a schematic illustration of the heart.

Anatomically, the heart includes a fibrous skeleton, valves, the trunks of the aorta, the pulmonary artery, and the muscle masses (myocardium) of the cardiac chambers (i.e., right and left atria and right and left ventricles). The schematically illustrated portions of the heart 10 shown in one or more of FIG. 3 or 6 include the right ventricle "RV" 20, the left ventricle "LV" 30, the right atrium "RA" 40 (the term "right atrium" herein including the superior vena cava and innominate vein), the left atrium "LA" 50 (and parts thereof), the superior vena cava 48, the coronary sinus "CS" 42, the great cardiac vein 44, the left pulmonary artery 45 (the term "left pulmonary artery" herein includes the main pulmonary artery and the right ventricular outflow tract), and the coronary sinus ostium or "OS" 41. FIG. 3 also illustrates the pulmonary veins 52 and neighboring regions. Other regions of interest may include the atrial septum, right and left atrial appendages, and the tricuspid annulus.

In certain embodiments, the atrial tissue targeted for ablation can include tissue in the pulmonary veins, such as at electrical focii residing therein, and/or the atrial muscle sleeves, which extend into the pulmonary veins. Other ablation regions of interest include one or both the vena cava of the right atrium.

The desired localized region(s) selected for placement of the local ablation source, typically electrodes, for ablating the heart according to the instant invention may vary depending on the physiology or ailment of the patient. The cardiac ablation source can be any suitable ablating technology including RF (radio-frequency), microwave, laser, cryogenic, radiation, ultrasound, chemical, and the like. As such, the local ablation source which contacts or delivers the ablation energy, power, or treatment to the tissue, can include one or transmitting electrodes as well as at least one sensing electrode. In some embodiments, the transmitting electrodes can also act as sensing electrodes. The ablation treatment and associated system or source can be configured to deliver any desired lesion geometry such as focal and/or linear. Further, the local ablation source, typically comprising at least one electrode, may be positioned in a number of regions and by a number of different techniques so that they are proximate to and/or in contact with the desired localized region of the myocardium.

For example, particularly for intercaval (intra-lumen or intra-cavity) applications, the electrodes can be held or positioned on a catheter which is sized and configured for insertion into the natural lumens of the heart (atriums, ventricles, veins, arteries, etc.). Other embodiments include ablation rods or other heating devices configured to ablate other areas of interest, such as in the pericardial space, on the outer surfaces of the cardiac walls. As such, the electrodes may be positioned into the body of the subject by surgical techniques or by inserting them using locating catheters holding same, and the like.

Examples of suitable ablation systems are described in the following U.S. Pat. Nos.:

| 6,042,580 | 5,492,119 | 5,662,606 | 5,364,352 | 5,666,970 |
| 5,681,280 | 6,099,524 | 5,606,974 | 5,741,320 | 5,857,997 |
| 5,596,995 | 5,735,280 | 6,050,994 | 6,059,778 | 6,049,737 |
| 6,045,550 | 5,810,740 | 5,617,854 | 5,971,980 | 6,146,381. |

The contents of these patents are hereby incorporated by reference as if recited in full herein.

Figure 5A:
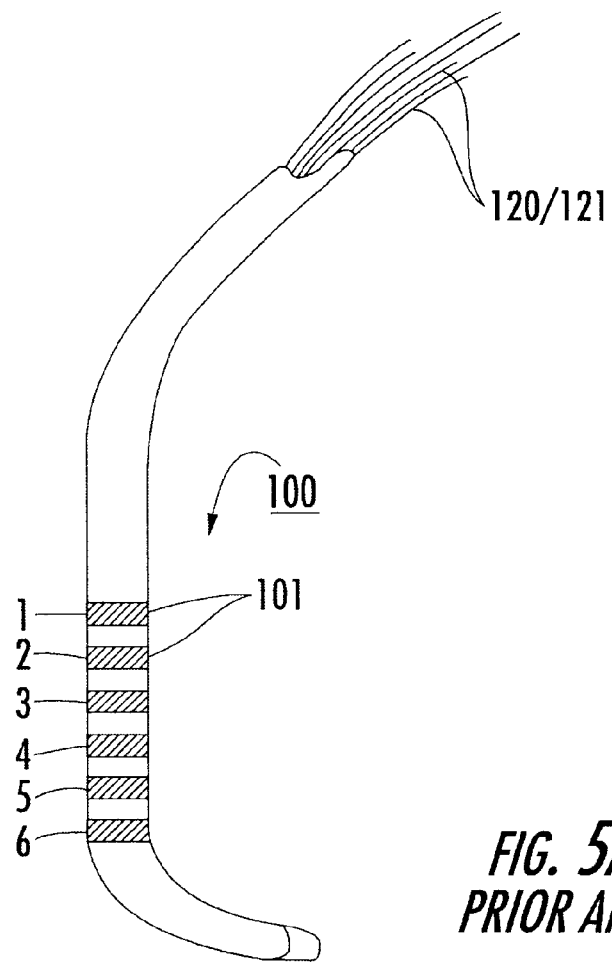
FIG. 5A is an enlarged partial cutaway view of a prior art ablation catheter having multiple electrodes which can be individually electrically decoupled or coupled as desired to provide sensing over different spatial regions of the lesion site according to embodiments of the present invention.
Figure 5B:
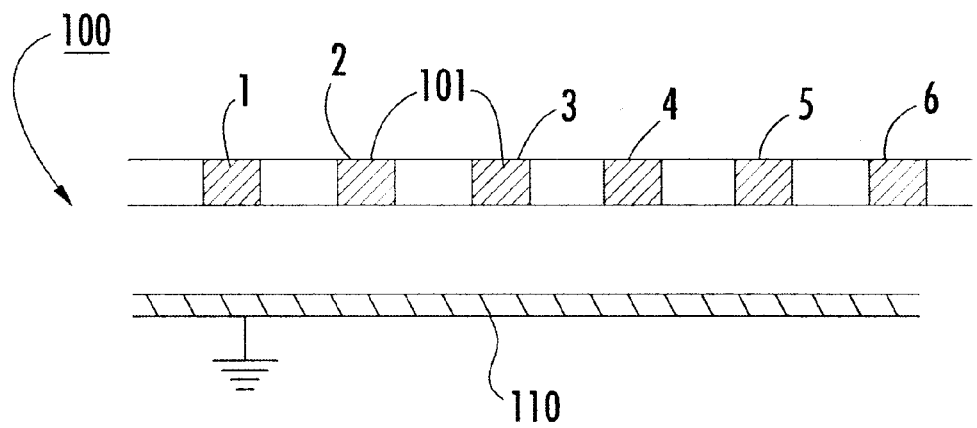
FIG. 5B is a schematic side section view of the electrodes of the catheter shown in FIG. 5A illustrating the prior art electrode and ground back plate operational configuration.

In certain embodiments, a linear ablation catheter including a plurality of discrete electrodes can be used to deliver RF energy to ablate the targeted tissue. See, e.g., Am. J. Cardiol. 1999; 83(5B): 227D–236D (which describes linear ablation catheters, sized at about 7 French in diameter which incorporate six or twelve 3 mm-long platinum band electrodes with an interelectrode spacing of 4 mm developed by Guidant Corporation located in Indianapolis, Ind.). The contents of this article are hereby incorporated by reference as if recited in f all herein. FIGS. 5A and 5B illustrate a catheter 100 with six bands of electrodes 101 (identified as electrode numbers 1–6).

For example, the electrode(s) can be held on a catheter and inserted into the endocardium or threaded through the heart and inserted into the veins in the heart (threaded through the OS and looped into the veins). In some embodiments, left or right atrial ablation (ablation of the endocardium proximate the left or right atrium (or both)) may be performed by locating an electrode(s) to extend in a portion of the left atrium and into the pulmonary vein(s) to help eradicate or control fibrillation activation in this region.

As noted above, the detecting or sensing of the electrogram measurements or signal associated with the lesion or lesion site can be obtained in a number of ways, including one or more dedicated sensing electrodes, or dual action transmitting and sensing electrodes whether unipolar, bipolar, or in combinations of different electrode bands and grounds on multi-pole catheters. Thus, the sensing is typically performed at at least one physical location along the lesion site (at the ablation source contact regions or adjacent necrosis regions associated therewith). In certain embodiments, the present invention can alter the electrical couplings of the individual electrodes to sense from and between different electrode couplings and thereby scan for additional information regarding the lesion efficacy along the length and thickness of the lesion during the ablation procedure. Thus, in certain embodiments, the electrodes may be switched to form different electrical couplings covering different spatial regions of the lesion as will be described further below.

Figure 2:
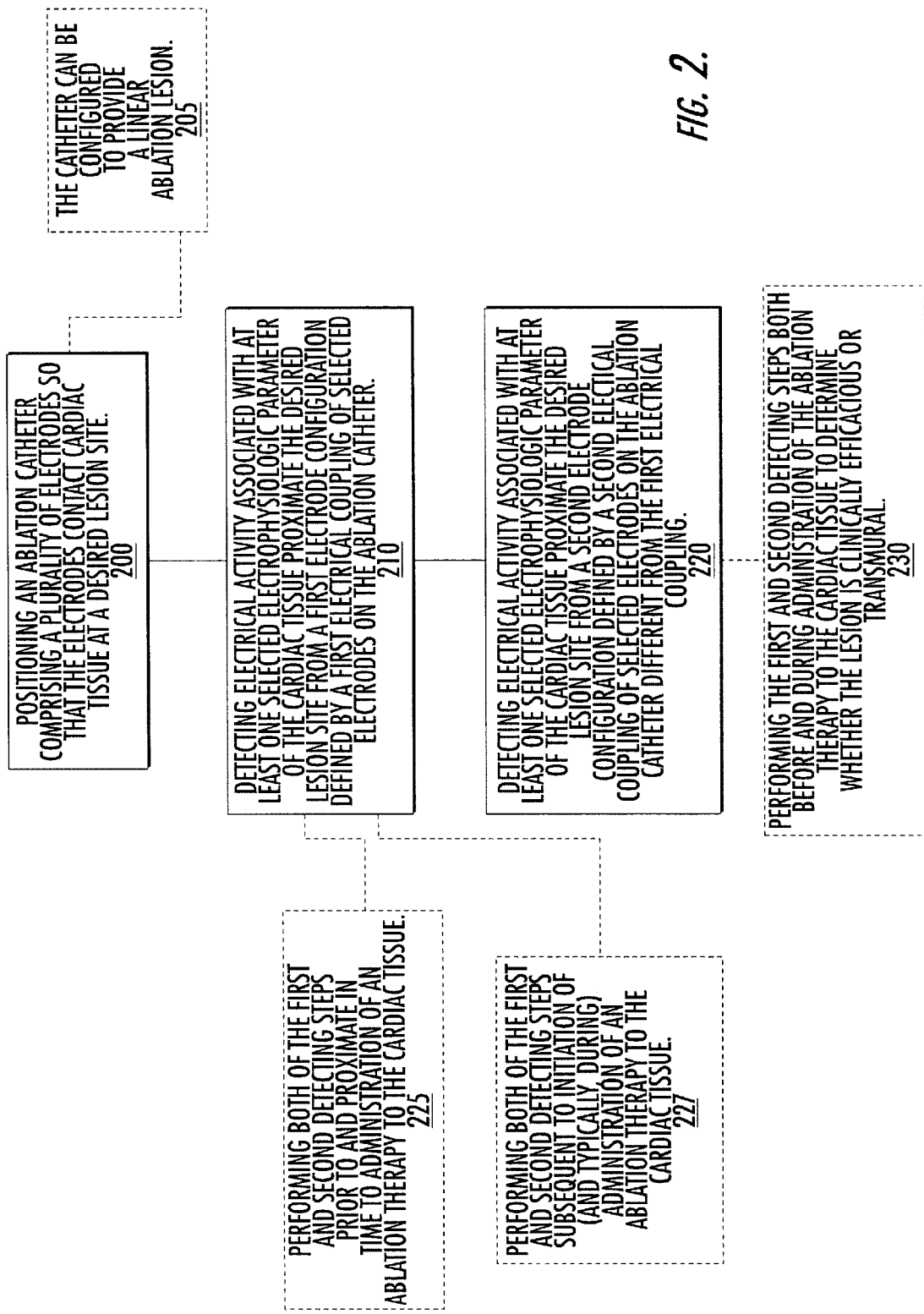
FIG. 2 is a block diagram of a method for detecting electrical activity associated with at least one electrophysiologic parameter of the cardiac tissue proximate the targeted or actual (ablated) lesion site according to embodiments of the present invention.

Referring to FIG. 2, in certain embodiments, an ablation catheter comprising a plurality of electrodes can be positioned so that the electrodes contact cardiac tissue at a desired lesion site (Block 200). As noted above, the catheter may be configured to generate a linear lesion (Block 205). The electrical activity associated with at least one selected electrophysiologic parameter of the cardiac tissue proximate the desired lesion site can be detected from a first electrode configuration defined by a first electrical coupling of selected electrodes (or a single electrode) on the ablation catheter (Block 210). This first electrical arrangement defines a first sensing configuration corresponding to a first region or spatial perspective of the underlying tissue about the lesion site. Then, the electrical activity associated with at least one selected eletrophysiologic parameter of the cardiac tissue proximate the lesion site can be detected from a second electrode configuration (Block 220). The second electrode configuration is defined by a second electrical coupling of selected electrodes on the ablation catheter different from the first electrode coupling. The two detecting steps can detect/use the same electrophysiologic parameter.

In certain embodiments, both of the detecting steps can be performed prior but proximate in time to the administration of an ablation therapy to the cardiac tissue (Block 225) and/or subsequent to initiation of (and typically during) administration of the ablation therapy to the cardiac tissue lesion site (Block 227). In some embodiments, the two detecting steps are performed both before and after initiation to determine whether the lesion is clinically efficacious or transmural (Block 230). This may allow a more reliable indicator of the condition of the lesion site over a larger volume when compared to conventional systems, as it can provide additional lesion site information about the extent of necrosis over larger spatial regions of the lesion site. However, as noted above, in certain embodiments, a single measurement taken after the treatment has been commenced may be sufficient to note whether the lesion is sufficiently transmural or clinically efficacious.

Thus, for example, the linear ablation catheter described above and shown in FIGS. 5A and 5B may include 6 different individually operable electrodes 101 and a ground plate 110 for the current return. In certain embodiments, the present invention contemplates switching electrical couplings between electrodes and scanning the data corresponding to the electrical signals sensed from a number of different electrode couplings. As shown in FIGS. 5A and 5B, the electrodes 101 can be serially numbered as electrode numbers 1–6. Thus, electrical signal data can be obtained from a plurality of the different combinations available by the electrical coupling of one, two or more electrodes to ground or to other electrodes (only a few such combinations are shown for illustration in Table 1 below). In certain embodiments, at least one unipolar, at least one bipolar, and at least one broader multi-electrode combination—both pre and post-initiation of the ablation therapy—can be used to obtain the data regarding the electrical activity of the lesion site.

TABLE 1

| EXAMPLES OF SENSING ELECTRODE COUPLINGS | |
|---|---|
| Pre-Ablation | Post-Initiation of Ablation |
| 1 + 2 + 3 + 4 + 5 + 6 → ground | 1 + 2 + 3 + 4 + 5 + 6 → ground |
| 1 + 2 + 3 + 5 + 6 → ground | 1 + 2 + 3 + 5 + 6 → ground |
| 1 + 2 + 3 → ground | 1 + 2 + 3 → ground |

TABLE 1-continued

| EXAMPLES OF SENSING ELECTRODE COUPLINGS | |
|---|---|
| Pre-Ablation | Post-Initiation of Ablation |
| 4 + 5 + 6 → ground | 4 + 5 + 6 → ground |
| 1 + 6 → ground | 1 + 6 → ground |
| 1 → ground (unipolar) | 1 → ground (unipolar) |
| 3 → 4 (bipolar) | 3 → 4 (bipolar) |
| 4 → 5 (bipolar) | 4 → 5 (bipolar) |

Regarding the particular parameter or parameters obtained and evaluated, as noted above, in each of the embodiments, the at least one electrophysiologic parameter can be (a) the same parameter (i.e., waveform of the amplitude of the detected signal) measured or evaluated in different ways or (b) a plurality of different parameters corresponding to the electrical activity of the tissue about the lesion site, obtained before, during and/or after ablation.

In other embodiments, the therapy can be individually adjusted (each electrode or electrode pairs whether unipolar or bipolar) or regionally adjusted (over a series of adjacent electrodes, e.g., electrodes 1–3 can define a first therapy zone and electrodes 4–6 can define a second therapy zone). "Adjusted" means that the electrode or electrode pairs or combinations can be activated, deactivated, or the ablation energy reduced or increased about the electrode(s) or region/therapy zone associated with the lesion site. This zone or individual adjustment or monitoring can be based on the broader sensing or monitoring capability provided by the instant invention. Thus, if the detected electrophysiologic signal is sufficiently reduced about the upper region or treatment zone, but not at the lower region or treatment zone, the system can selectively activate the local electrodes positioned in the lower region, which is not indicating sufficient reduction. Alternatively, the detected condition may indicate a reduced power or temperature at one or more electrodes or regions, and the present invention may selectively increase the power or temperature at the identified discrepant or low region or electrode.

Figure 4:
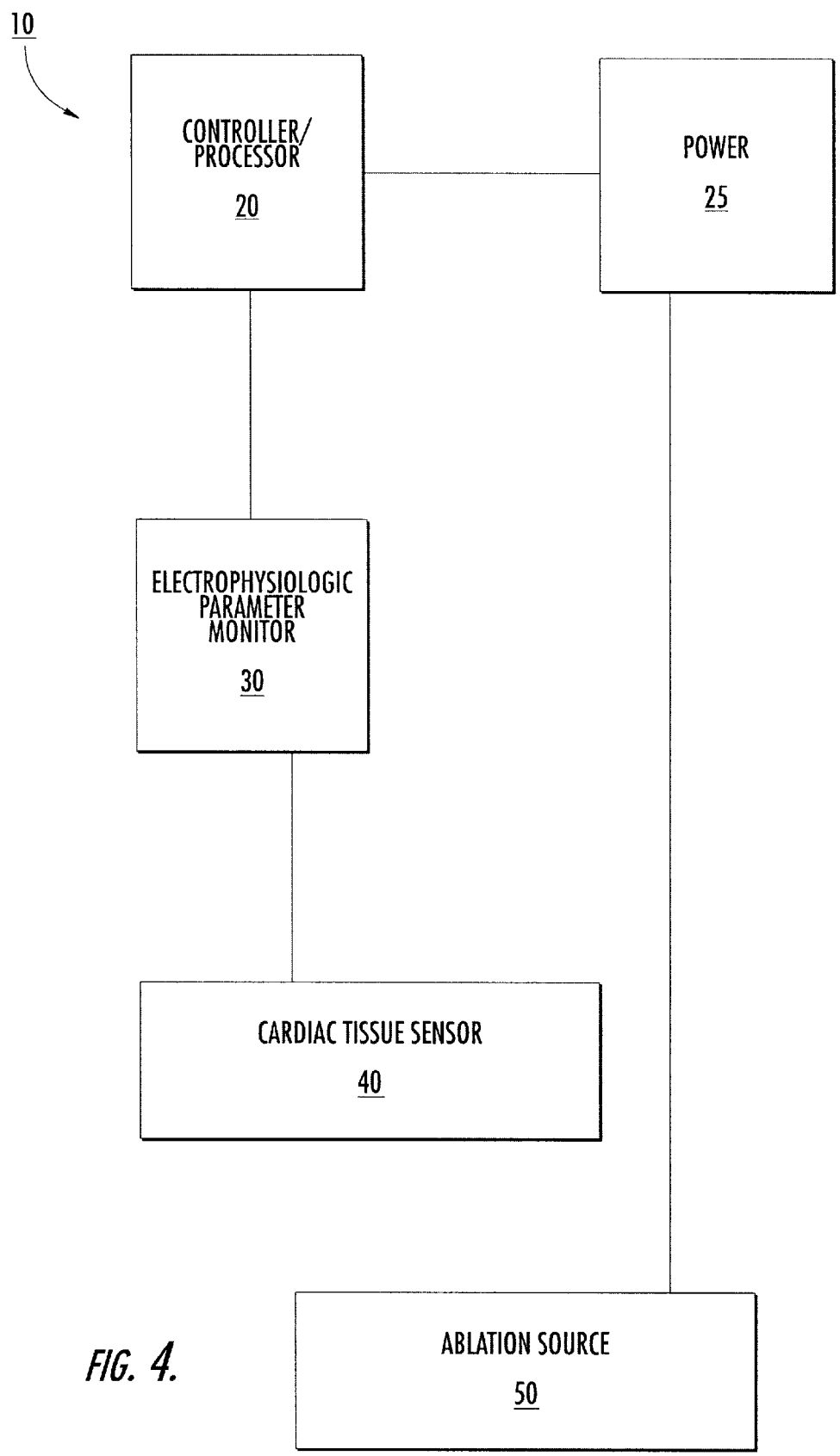
FIG. 4 is a schematic illustration of a cardiac ablation system according to embodiments of the present invention.

Turning now to FIG. 4, the system 10 can include a controller/processor 20, a power source 25, and an electrophysiologic activity monitor 30 (which may be combined with the controller/processor) is configured to receive the signal and analyze the associated data relayed from the lesion site of the cardiac tissue. The system 10 also includes a cardiac tissue sensor 40 and an ablation source 50. The ablation source 50 may include a remote and local portion, the local portion being adapted to contact the cardiac tissue at the desired lesion site and the remote portion being configured to generate or deliver the associated signal or energy to the local portion. As noted above, the cardiac sensor 40 may be provided by an ablation electrode or may be a separate dedicated sensing electrode(s). As also noted above, the ablation source 50 can be any desired ablation source generated by any suitable ablation technology.

The controller/processor 20 may be configured as any suitable data processing system capable of carrying out the operations described herein for controlling data flow, analyzing the data, and providing communications with the components of the system 10. Thus, the data processing system may be a general purpose data processing system, such as a personal computer, a specialized data processing system such as a digital signal processor or embedded microprocessor, a network appliance, such as a micro web server, a pervasive computing device such as a personal digital assistant, or the like.

As noted above, in certain embodiments, catheters can be used to hold an electrode or series of point or line electrodes in a desired arrangement or to position them in location within the lumens of the heart proximate desired myocardium regions. For example, in some embodiments catheters which are insertable into the heart (typically through the superior or inferior vena cava) without the need for surgical incision. The term "catheter" as used herein includes a "stylet" as known to those of skill in the art. The term "lead" indicates that at least one electrical line extends to the electrode. The catheter may hold electrodes and leads. Of course, in certain embodiments a lead with its associated electrode(s) may be used independently of a catheter, depending on the application/resident position.

Figure 6:
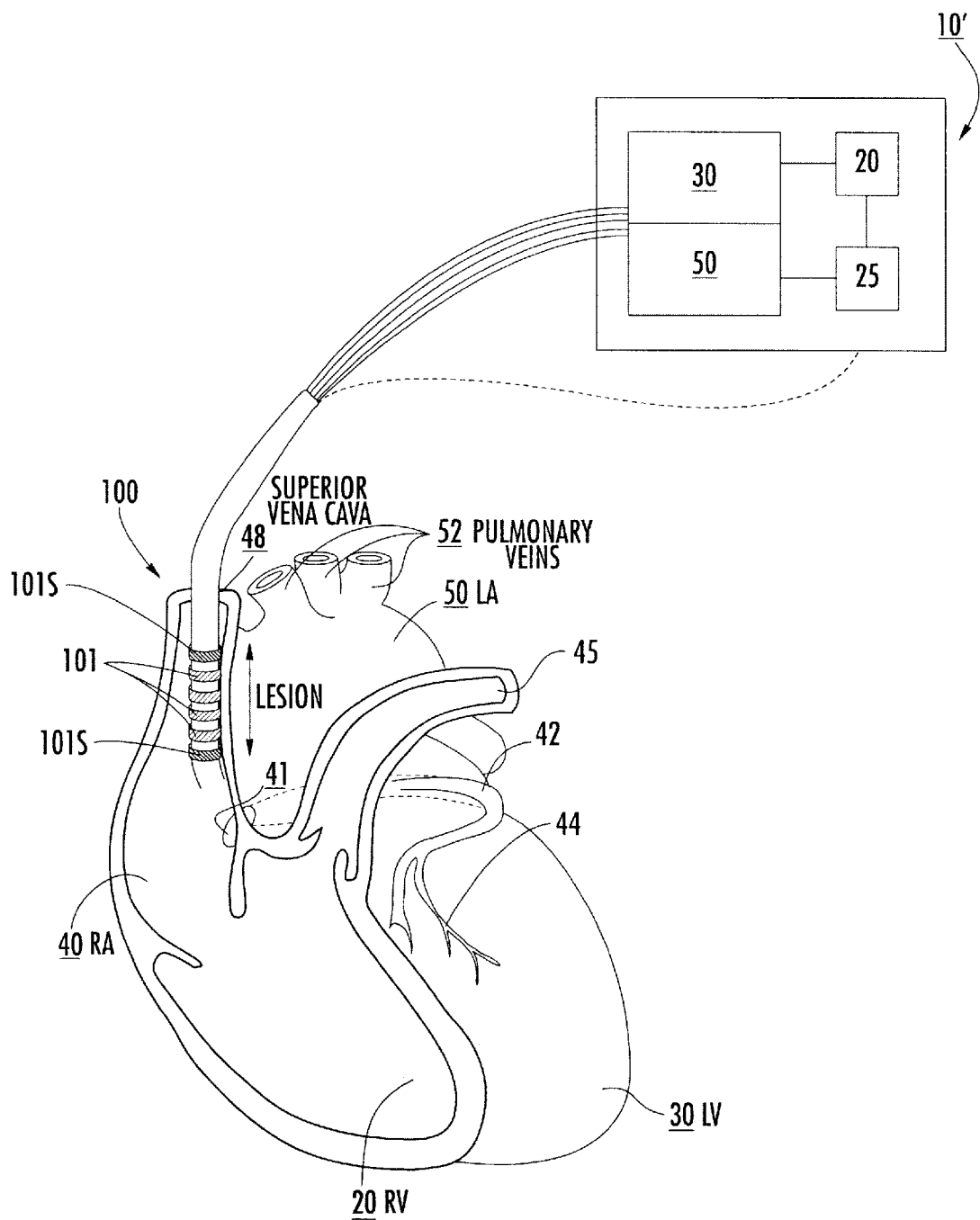
FIG. 6 is a schematic illustration of the heart illustrating an ablation system with an ablation catheter positioned to ablate local cardiac tissue according to embodiments of the present invention.

FIG. 6 illustrates an intracaval ablation catheter 100 with a plurality of electrodes 101 and two "dedicated" sensing electrodes 101s inserted into the heart to provide a lesion (depicted by the letter "L"). The dedicated sensing electrodes 101s are located about the transmitting electrodes 101 so as not to disrupt the continuity of the lesion provided by same. The system 10' can include the power source 25, controller/processor 20 and electrophysiologic activity detector/analyzer 30 as well as an ablation source 50 which are operably associated with the sensing electrodes 101s and the transmitting electrodes 101. A switch may be used to direct the incoming or outgoing signal path depending on whether a receive or transmit mode is operable (not shown).

Figure 7:
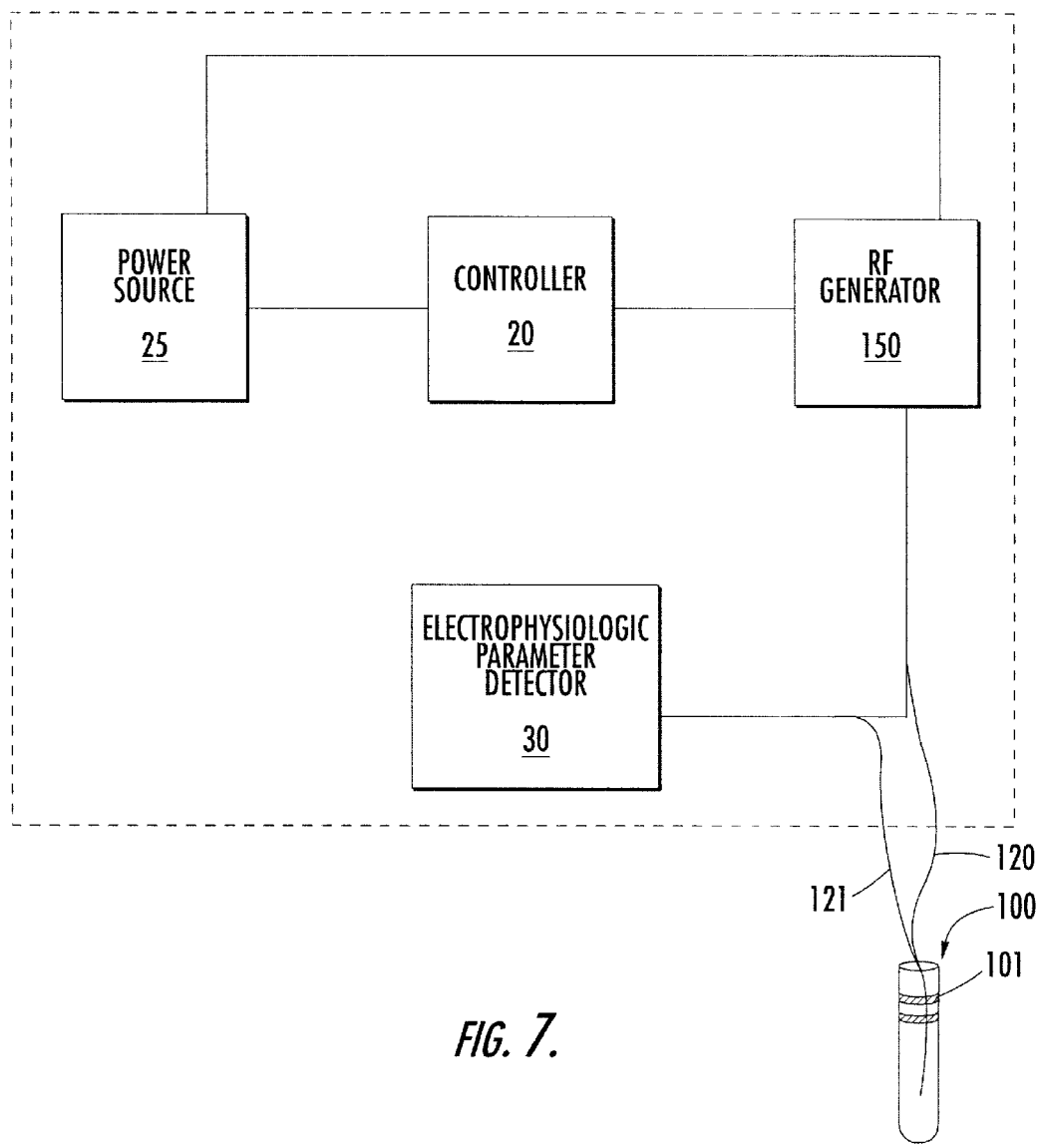
FIG. 7 is a schematic illustration of a RF ablation system according to embodiments of the present invention.

FIG. 7 illustrates certain embodiments of the invention which include electrodes 101 held on a catheter 100 which are operably associated with an RF signal generator 150 and a power source 170 which, during operation, supplies the RF signals/ablation energy to the electrodes 101 at the desired lesion site of the myocardium. The transmitting lead 120 as well as the receiving (sensing) lead 121 are shown for clarity as a single lead recognizing that, typically, each electrode will have at least one lead associated therewith, and the transmitting and receiving lead may be a single lead able to relay signals in both directions.

The flowcharts and block diagrams of FIGS. 1, 2, 4 and 7 illustrate the architecture, functionality, and operation of possible implementations of systems, methods and computer program products for various embodiments of the present invention. In this regard, each block in the flow charts or block diagrams may represent a module, segment, or portion of code, which comprises one or more executable instructions for implementing the specified logical act(s). It should also be noted that, in some alternative implementations, the acts noted in the blocks may occur out of the order noted in the figures. For example, two blocks shown in succession may, in fact, be executed substantially concurrently, or the blocks may sometimes be executed in the reverse order, depending upon the functionality involved.

It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, embedded processor or other programmable data processing apparatus to produce a machine, such that the instructions, which execute via the processor of the computer or other programmable data processing apparatus, create means to and implementing circuits configured to implement the functions specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart and/or block diagram block or blocks.

The present invention is further explained in the following non-limiting Examples.

EXAMPLES

Seven animals were used in an investigation directed to evaluating when an ablation lesion may be considered clinically efficacious, based on a review of a number of different parameters. In the experiment, the intercaval lesion length and width along the endocardium were 32±8 mm and 5±1 mm, respectively. Histologically, the presence or absence of transmural myocardial necrosis was determined at each electrode position along the length of each lesion. Overall, transmural necrosis was present in 25 out of a total of 42 "unipolar sites" (beneath electrodes), and in 14 out of a total of 35 bipolar sites (beneath and between electrodes). The post- vs. pre-ablation percent change in PTs and EAAs and the time that the ablation electrodes were >50° C. during RF energy delivery for electrodes adjacent to transmural and non-transmural necrosis are shown in Table 2 below. All of the variations in these values were significantly different, both in unipolar and bipolar modes.

TABLE 2

| | NSR PT increase (%) | | NSR EAA decrease (%) | | AF EAA decrease (%) | | Time >50° C. (s) | |
|---|---|---|---|---|---|---|---|---|
| | transmural | non-trans. | transmural | non-trans. | transmural | non-trans. | transmural | non-trans. |
| unipolar | 379 ± 103 | 207 ± 93 | 48 ± 19 | 15 ± 20 | 33 ± 11 | 22 ± 14 | 385 ± 186 | 139 ± 132 |
| bipolar | 379 ± 80 | 259 ± 60 | 63 ± 17 | 42 ± 19 | 63 ± 9 | 43 ± 15 | 346 ± 113 | 107 ± 102 |

The data in Table 2 shows that significant differences in PTs, EAAs, and durations of lethal temperatures exist from electrodes adjacent to transmural vs. non-transmural necrosis during the creation of linear lesions. Furthermore, with these data, cut-off criteria, or combinations of cut-off criteria, of these measures may be established in order to prospectively identify lesion regions as transmural or non-transmural. For example, using bipolar criteria of an EAA reduction in AF of >50% and an ablation electrode duration of at least 240 s at >50° C., one finds, retrospectively, a sensitivity for transmural regions of 93% (13/14) and a specificity of 95% (20/21).

Background

Recently, the reduction in electrogram activation amplitude (EAA) from the ablation catheter electrodes measured in NSR or during a paced rhythm has been correlated with successful lesion creation in isolated tissue preparations as well as in animal models. See Avitall et al., The creation of linear contiguous lesions in the atria with an expandable loop catheter, J. Am Coll. Cardiol. 1999;33(4):972–984; Gepstein et al., Atrial linear ablations in pigs. Chronic effects on atrial electrophysiology and pathology, Circulation 1999;100(4):419–426; Liem et al., Electrophysiological correlates of transmural linear ablation, Pac. Clin. Electrophysiol. 2000;23:40–46; and Nakagawa et al., Use of atrial potential attenuation to identify endpoint of radiofrequency application for continuous, transmural linear atrial ablation, Circulation (abstract) 1997; 96:I-451.

The use of EAA reduction may be particularly promising in situations when temperature measurements correlate poorly with lesion formation (i.e. when RF is delivered in areas of poor blood flow), or when assessment of conduction block is difficult (i.e. in the left atrium) or impossible (i.e. during AF).

During the catheter maze ablation procedure, the myocardial substrate is electrically compartmentalized into regions sufficiently small that AF may not be maintained. It has been recently documented that for the creation of conduction block across a linear lesion in atrial myocardium, transmural necrosis is almost always required. See Taylor et al., High-resolution mapping and histologic examination of long radiofrequency lesions in canine atria, J Cardiovasc. Electrophysiol. 1999;10:1467–1477.

The investigation, thus, sought to assess the predictive value of electrophysiologic and thermal measures in identifying regions along linear ablation lesions as being transmural or non-transmural. The three electrophysiologic measures investigated were the increase in pacing threshold (PT) in NSR, the decrease in EAA in NSR, and the decrease in EAA in AF; the thermal measures investigated were the duration that the ablation electrodes were maintained above certain temperatures during RF energy delivery.

Methods

Model: A sheep model was selected to conduct the investigation, primarily because of the similarity of its heart to that of the human, and also because of the laboratory's experience with an acute model of AF in this species. AF was induced by burst pacing with a dedicated pacing lead in the right atrial appendage and maintained by a titrated, continuous infusion of acetyl-$\beta$-methylcholine chloride in the intrapericardial space. The drug was administered through a very small (hypodermic-needle sized) incision made in the chest wall just inferior to the sternum; the chest remained closed. As necessary, AF was cardioverted and NSR restored externally.

Experimental set-up: In the anesthetized dorsally recumbent animal, a 6-pole GUIDANT HRT linear ablation catheter was positioned between the superior and inferior vena cavae along the atrial septum, under which the endocardial myocardium is smooth. Along with requisite pair of cutaneous ground pads, situated beneath the animal, the catheter was interfaced through a specialized junction box to a GUIDANT HRT phased radio-frequency (RF) ablation generator and associated data logger. The specialized junction box allowed the tapping of 11 electrograms from the 6 electrodes from the ablation catheter (6 unipolar and 5 bipolar electrograms), which were displayed on the laboratory data acquisition system. The catheter position was adjusted so as to maximize the amplitude of the sinus A waves.

Pre-ablation data acquisition: Once the catheter position was optimized, a 2-minute epoch of the 11 electrograms in NSR was recorded. Also in NSR, cathodal unipolar and bipolar current PTs were determined for the ablation catheter electrodes with pacing stimuli of 2.0 ms; these pacing thresholds were determined using a standard step-up, step-down protocol. In AF, a 10-minute period(s) of the 11 electrograms was recorded.

Ablation Protocol: After acquiring the pre-ablation electrophysiologic data, the ablation portion of the protocol was begun. Ablation was performed under automatic temperature control mode (ATC) set to 62° C. with a power limitation of 12 W. Initially, one 180-s RF energy application was delivered to all 6 electrodes. After this initial application, two minutes of the electrograms in NSR were evaluated. If the A-wave amplitudes of all 6 unipolar and 5 bipolar electrograms were reduced by $\geq 80\%$ compared to their pre-ablation amplitudes, no more ablation was performed. If this amplitude reduction criterion was not met, another 180-s RF energy delivery was performed, after which the 11 egrams were once again evaluated. If still the amplitude reduction criteria were not met, one last 180-s RF energy application was delivered. This third RF application was the last, even if the amplitude reduction criteria still went unmet. The selection of $\geq 80\%$ A-wave amplitude reduction as an appropriate endpoint for lesion creation was based on previous reports (Nakagawa et al., 1997; Gepstein et al., 1999, supra).

Ablation data acquisition: During RF energy delivery, the GUIDANT HRT data logger recorded the temperature from the thermocouples of the ablation electrodes every second.

Post-ablation data acquisition: After the ablation protocol, a 2-minute epoch of the 11 electrograms was recorded in NSR; also in NSR, unipolar and bipolar PTs were determined for the ablation catheter electrodes in an identical manner as they were acquired prior to the ablation protocol. In AF, the 11 electrograms were recorded for 10 minutes.

Lesion assessment. After animal euthanasia, the heart was excised. The location of the ablation electrodes was recorded. The right atrium was isolated and stained with 2,3,5-triphenyl-tetrazolium chloride (TTC). The endocardial dimensions of the linear ablation lesion were measured. The right atrium was then fixed in 10% phosphate-buffered formalin for >24 hrs. After fixation, the tissue was sectioned perpendicular to the long axis of the ablation lesion approximately every 3 mm, obtaining at last one cross-section from the myocardium that was under each of the ablation electrodes and between neighboring ablation electrode pairs. Sections were embedded in paraffin, cut at 5-$\mu$m thickness, and stained with hematoxylin and eosin or Gomorri aldehyde fuchsin trichrome. (Taylor et al., 1999). A section was classified as transmural when myocardial necrosis was noted to extend from the endocardial to the epicardial layer. Each linear lesion was considered to consist of 6 unipolar sites (one for each electrode) and 5 bipolar sites (one for each pair of neighboring electrodes). Each site was evaluated according to the presence or absence of transmural necrosis. For unipolar analysis, a site was classified as transmural if the section(s) under the electrode was transmural. For bipolar analysis, a site was considered transmural when the sections under and between each electrode pair were transmural. For unipolar lesion regions that were judged to have not been transmural, the mean thickness of the lesion region was determined.

Electrogram activation amplitude measurement: An electrogram activation amplitude (EAA) was assessed for each recorded epoch (pre-ablation and post-ablation, each in NSR and AF) for each of the 11 electrograms (6 unipolar and 5 bipolar). In NSR, this EAA was defined to be the average of five A wave amplitudes (in mV), each one being measured from the pre-activation electrogram baseline to the peak of the local A wave activation.

In AF, there are no intrinsic, well-defined activations; therefore, the EAA was defined to be the standard deviation of the electrogram over a 10 second period (also in mV). The test duration of 10 seconds was selected through analyses in which the standard deviation of electrograms was plotted for a variety of durations; a duration of 10 s was the shortest that was consistently not significantly different from those of longer durations. Unipolar electrograms were fraught with far-field ventricular activations (R waves). For EAA determinations in NSR, these R waves could be easily excluded visually. In AF, any contribution to the EAA was eliminated in unipolar electrograms by excluding an interval of 160 ms surrounding the peak of each surface (lead II) R wave.

Study design: The post- vs. pre-ablation electrophysiologic changes (PTs and EAA in NSR and EAAs in AF) and the durations during RF energy delivery that the catheter electrodes were maintained above certain temperature thresholds were independently grouped based on whether they arose from electrodes adjacent to transmural or non-transmural lesion regions and compared with two-tailed Student's-t tests. Differences were deemed significant if $p<0.05$.

Results

Seven sheep ($62\pm3$ kg) completed the linear ablation protocol, and therefore the data from a total of 7 linear lesions were analyzed.

Ablation catheter placement: In contrast to humans, the posterior intercaval region of the sheep has a myocardial tubercle that makes this region convex and thus suboptimal for linear ablation with currently available GUIDANT HRT catheters. For this reason, the ablation catheter was situated along the septal side (medial with respect to the heart) of the posterior intercaval region, where the tubercle was less pronounced in most sheep. In some sheep, the intercaval distance was not long enough to support all 6 catheter electrodes; indeed, post-mortem inspection revealed that the end electrodes were sometimes, to differing extents, extended into the SVC and IVC. In every animal, the catheter electrodes were attempted to center to the myocardial intercaval tissue as much as possible, relying mostly on "balancing" EAAs across the catheter electrodes.

PTs and EAAs prior to ablation: In NSR, unipolar and bipolar PTs were $1.15\pm0.31$ mA and $1.33\pm0.94$ mA, respectively; EAAs in NSR were $2.93\pm1.74$ mV and $3.67\pm0.80$ mV, respectively. In AF, the standard deviation of the unipolar electrograms after excluding far-field R waves was $0.56\pm0.26$ mV. EAAs in AF in bipolar mode were $0.57\pm0.80$ mV.

Ablation: All animals underwent the maximum of 3 RF energy applications, as no ablation lesion presented an EAA reduction in NSR of all 11 electrograms of $\geq 80\%$ relative to their pre-ablation amplitudes.

Ablation lesion characteristics: After TTC staining, four out of the seven intercaval lesions were found to be continuous along the endocardium; the lesions from the other 3 animals evidenced endocardial discontinuities (gaps). The mean lesion length was $32\pm8$ mm, with a mean width of $5\pm1$ mm. On histological evaluation, 25 out of a total of 42 unipolar sites and 14 out of a total of 35 bipolar sites were determined to be transmural. The average lesion depth for the non-transmural sites was $1.4\pm1.3$ mm (range: 0–4.1 mm).

Figure 8A:
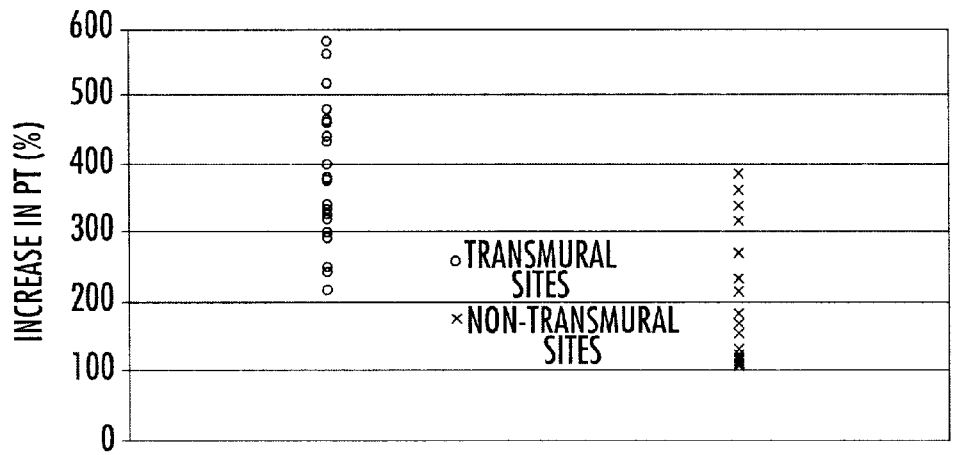
FIG. 8A is a graph illustrating the percent increase in unipolar pacing threshold at each electrode site measured after ablation according to embodiments of the present invention.
Figure 8B:
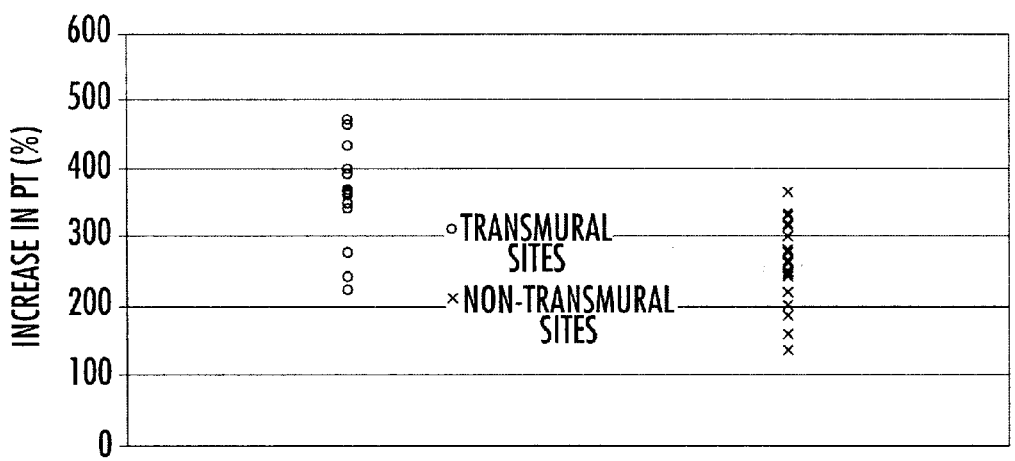
FIG. 8B is a graph illustrating the percent increase in bipolar pacing threshold at each electrode site measured after ablation according to embodiments of the present invention.

PTs after ablation: In NSR, the PTs were increased by the presence of the ablation lesions, to $3.23\pm1.12$ mA (unipolar) and $3.90\pm0.95$ mA (bipolar). The percentage increases in post- versus pre-ablation PTs was $310\pm130\%$ (unipolar) and $303\pm87\%$ (bipolar). Shown in the FIGS. 8A and 8B graphs below are the unipolar (FIG. 8A) and bipolar (FIG. 8B) PT increases from electrodes that were adjacent to tissue necrosis that was transmural (o) and non-transmural (x). The unipolar PT increase of electrodes adjacent to transmural necrosis was $379\pm103\%$, while that for electrodes adjacent to non-transmural necrosis was $207\pm93\%$; this difference was statistically significant ($p<0.05$). Similarly, the bipolar PT increase was greater for those electrode pairs adjacent to transmural necrosis ($370\pm80\%$) versus non-transmural necrosis ($259\pm60\%$).

Figure 9A:
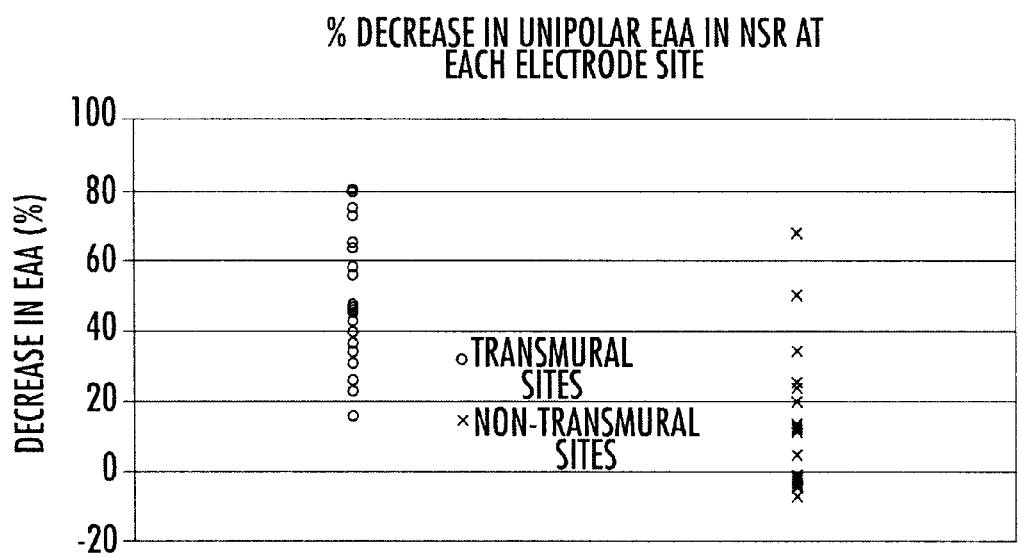
FIG. 9A is a graph illustrating the percent decrease in unipolar electrogram activation amplitude (EAA) in normal sinus rhythm (NSR) at each electrode site measured after ablation according to embodiments of the present invention.
Figure 9B:
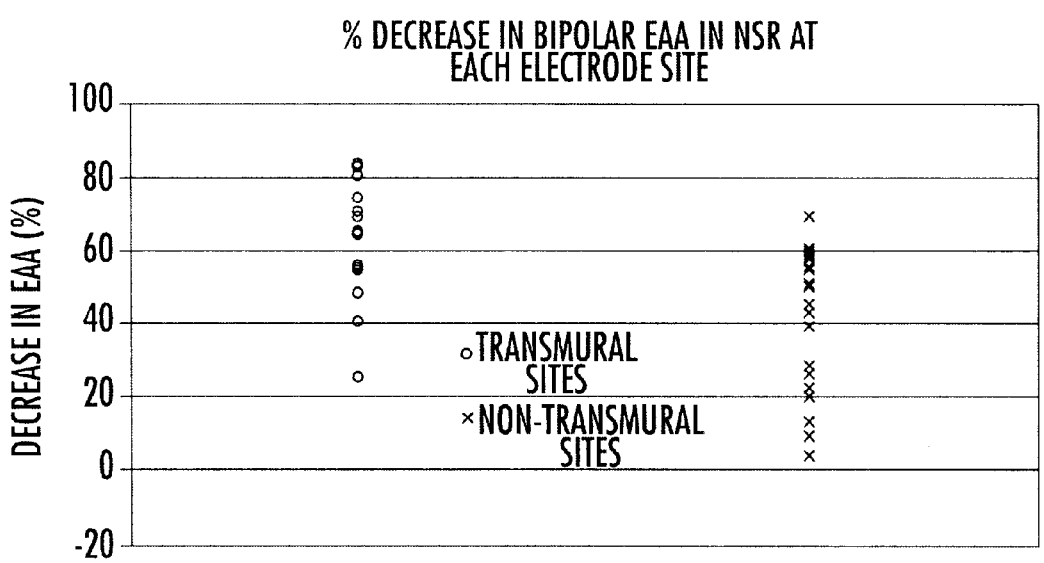
FIG. 9B is a graph illustrating the percent decrease in bipolar EAA in NSR at each electrode site measured after ablation according to embodiments of the present invention.

EAAs in NSR after ablation: Unipolar and bipolar EAAs in NSR were reduced after the creation of the ablation lesions. In unipolar mode, the NSR EAAs were reduced to $1.66\pm0.76$ mV ($p<0.05$ compared to pre-ablation level); in bipolar mode, the NSR EAAs were reduced to $1.62\pm0.81$ mV ($p<0.05$ compared to pre-ablation level). This corresponded to an overall decrease in EAA in NSR of $35\pm26\%$ (unipolar) and $50\pm21\%$ (bipolar). Shown in FIGS. 9A and 9B are the unipolar (FIG. 9A) and bipolar (FIG. 9B) EAA decreases in NSR from electrodes that were adjacent to tissue necrosis that was transmural (o) and non-transmural (x). The unipolar EAA decrease of electrodes adjacent to transmural necrosis was $49\pm19\%$, while that for electrodes adjacent to non-transmural necrosis was $15\pm20\%$; this difference was statistically significant ($p<0.05$). Similarly, the bipolar EAA decrease was greater for those electrode pairs adjacent to transmural necrosis ($63\pm17\%$) versus non-transmural necrosis ($42\pm19\%$).

Figure 10A:
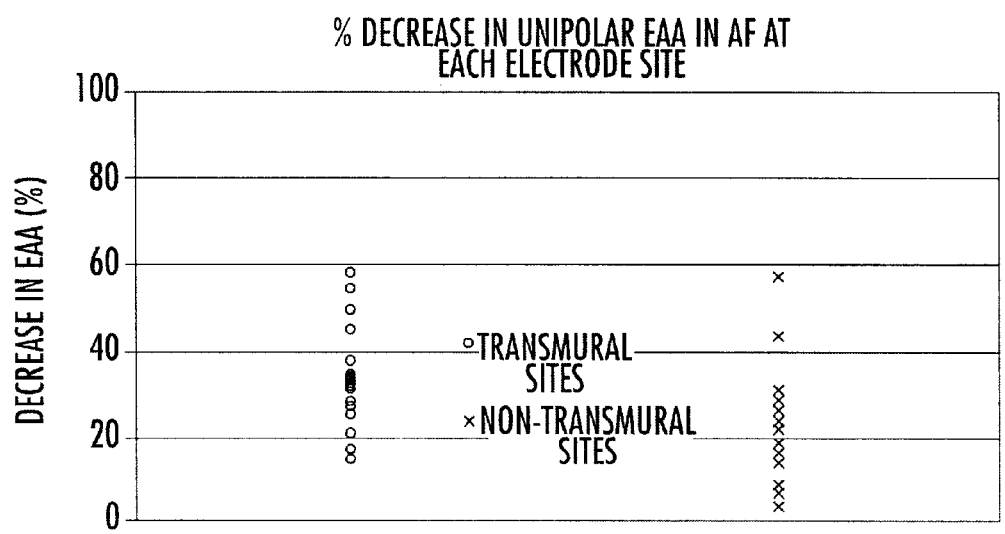
FIG. 10A is a graph illustrating the percent decrease in unipolar EAA in atrial fibrillation (AF) at each electrode site measured after ablation according to embodiments of the present invention.
Figure 10B:
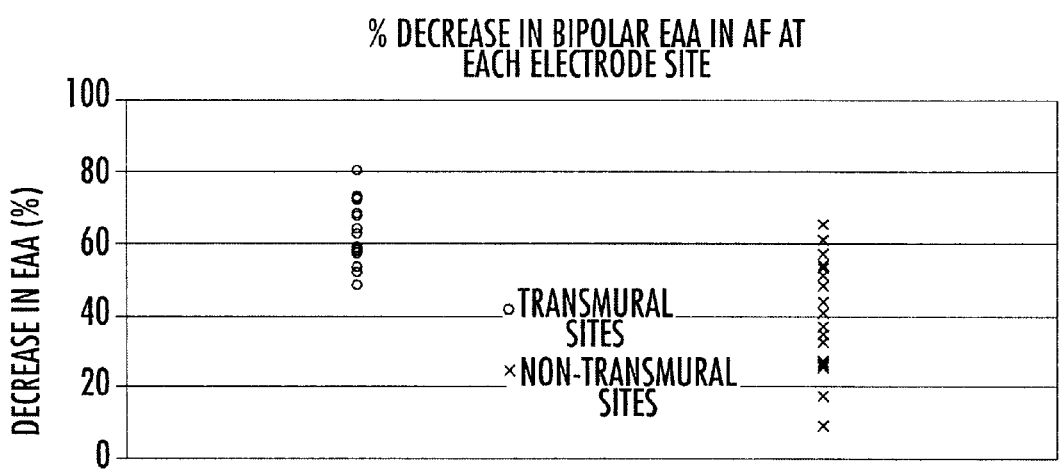
FIG. 10B is a graph illustrating the percent decrease in bipolar EAA in AF at each electrode site measured after ablation according to embodiments of the present invention.

EAAs in AF after ablation: As in NSR, the EAAs in AF after the presence of the ablation lesions were reduced compared to the pre-ablation levels; this was true for electrograms in both unipolar and bipolar modes. In unipolar mode, the reduction was to $0.39\pm0.19$ mV post-ablation ($p<0.05$ compared to pre-ablation level); in bipolar mode, the EAAs in AF were reduced to $0.25\pm0.08$ mV post-ablation ($p<0.05$ compared to pre-ablation level). This corresponded to an overall decrease in EAA in AF of $29\pm13\%$ (unipolar) and $51\pm16\%$ (bipolar). FIGS. 10A and 10B illustrate the unipolar (FIG. 10A) and bipolar (FIG. 10B) EAA decreases in AF from electrodes that were adjacent to transmural (o) and non-transmural (x) tissue necrosis. The unipolar EAA decrease in AF of electrodes adjacent to transmural necrosis was $33\pm11\%$, while that for electrodes adjacent to non-transmural necrosis was $22\pm14\%$; this difference was statistically significant ($p<0.05$). Similarly, the bipolar EAA decrease in AF was greater for those electrode pairs adjacent to transmural necrosis ($63\pm9\%$) versus non-transmural necrosis ($43\pm15\%$).

Ablation electrode time above certain temperatures: From the ablation system data logger, the amount of time was determined (number of seconds) during RF energy delivery that each electrode spent above certain temperatures.

Figure 11A:
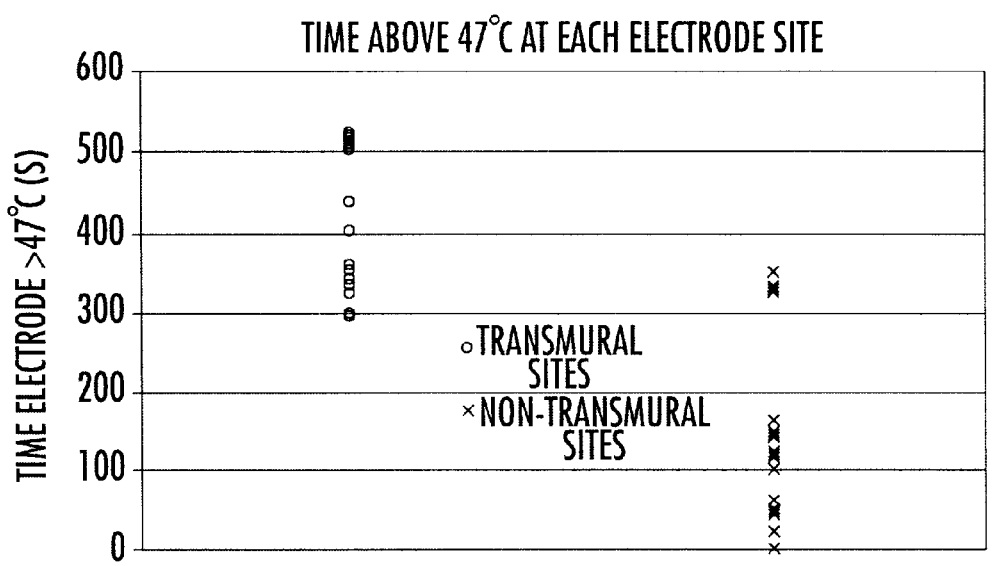
FIG. 11A is a graph illustrating the time of exposure to temperatures above 47° C. at each electrode site measured after ablation according to embodiments of the present invention.
Figure 11B:
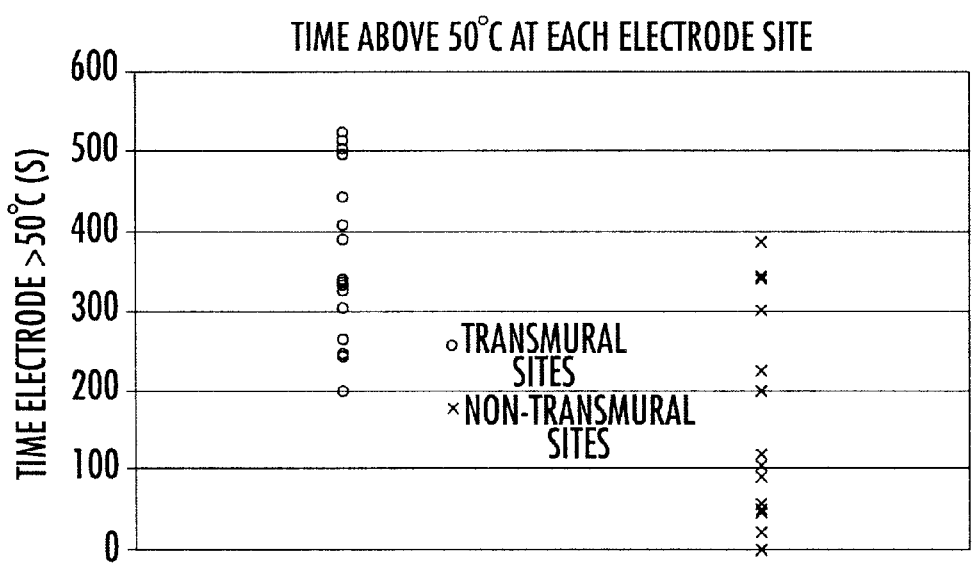
FIG. 11B is a graph illustrating the time of exposure to temperatures above 50° C. at each electrode site measured after ablation according to embodiments of the present invention.

FIGS. 11A and 11B show the amount of time that electrodes spent above 47° C. and 50° C.; these data are broken down into those electrodes that were adjacent to transmural necrosis and those electrodes that were adjacent to non-transmural necrosis. It should be noted that several of the electrodes sites in the development of the lesions may have not reached those temperatures, and therefore these data are shown in the graphs below as zero. In the 47° C. graph (FIG. 11A), the mean time spent >47° C. for the sites adjacent to transmural necrosis was 442±87 s, with all 25 of these electrode sites reaching the required temperature; the amount of time spent >47° C. for the sites adjacent to non-transmural tissue necrosis was 123±115 s (including 2 of the 17 electrode sites never reaching the required temperature), which was significantly less. In the 50° C. graph (FIG. 11B), the mean time spent >50° C. for the sites adjacent to transmural necrosis was 385±106 s, with all 25 of these electrode sites reaching the required temperature; the amount of time spent >50° C. for the sites adjacent to non-transmural necrosis was 139±132 s (including 3 of the 17 electrode sites never reaching the required temperature), which was significantly less. It is also worth noting that the mean maximum temperature recorded by the data logger for electrodes adjacent to transmural necrosis was 61±3° C.; that for electrodes adjacent to non-transmural necrosis was 53±7° C., which was significantly lower.

Figure 12A:
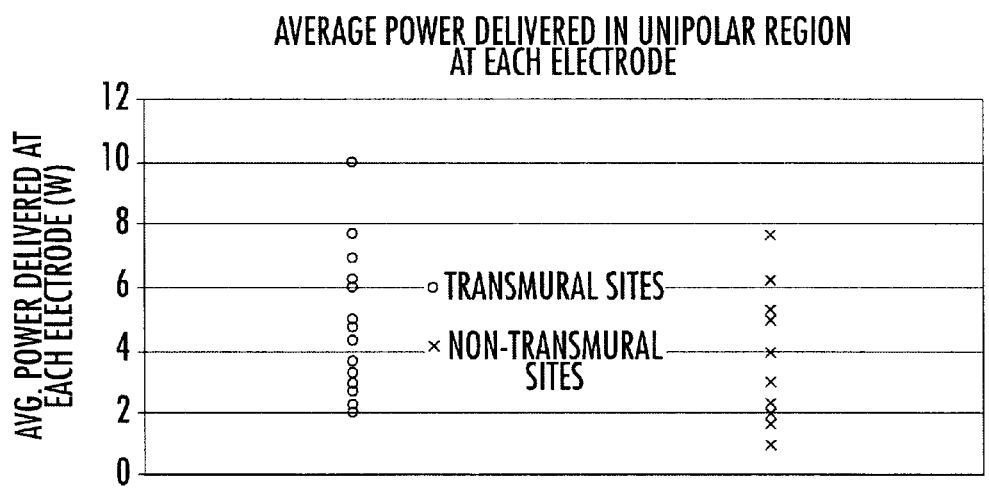
FIG. 12A is a graph of the average power delivered in a unipolar region at each electrode after ablation according to embodiments of the present invention.
Figure 12B:
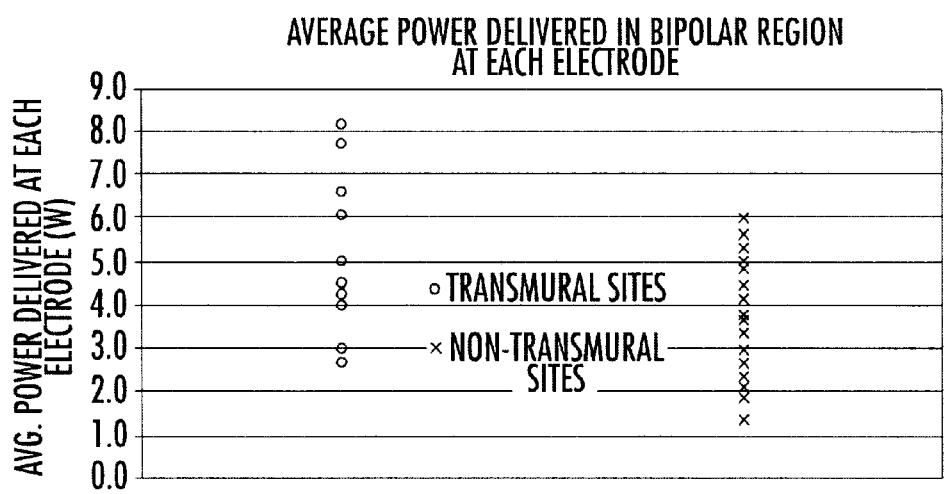
FIG. 12B is a graph of the average power delivered in a bipolar region at each electrode according to embodiments of the present invention.

Lesion transmurality at different ablation power deliveries: From the ablation system data logger, the average power delivered to each ablation electrode during lesion creation was determined. The average power delivered to each ablation site was then grouped as to whether the lesion region was transmural or not. FIGS. 12A and 12B show these data sets. FIG. 12A shows the average delivered power to ablation electrodes adjacent to unipolar transmural and nontransmural lesion regions, and FIG. 12B shows the same to bipolar transmural and nontransmural lesion regions. The mean average power delivered to all of the electrodes was 4.2±2.0 W. For the electrodes adjacent to unipolar transmural lesion regions, the mean average power delivered was 4.7±2.0 W, and for the nontransmural lesion regions, it was 3.5±2.0 W; this difference exhibited a strong trend toward being significantly different (p=0.06). When judged relative to bipolar transmurality, the average power delivered to transmural lesion regions was 4.8±1.8 W, while that delivered to nontransmural lesion regions was 3.6±1.4 W; these two data sets were found to be significantly different.

Figure 13A:
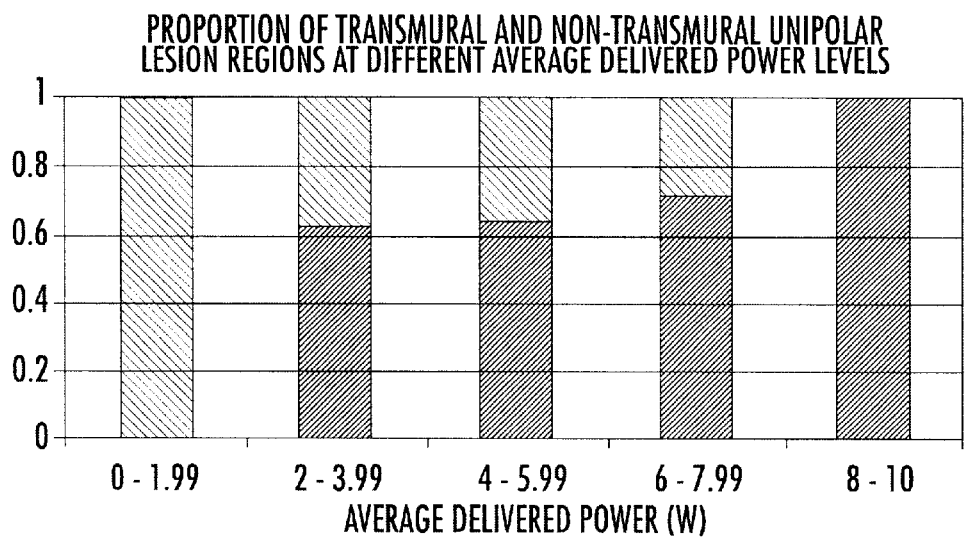
FIG. 13A is a graph of the proportion of transmural and non-transmural unipolar lesion regions at different average delivered power levels according to embodiments of the present invention.
Figure 13B:
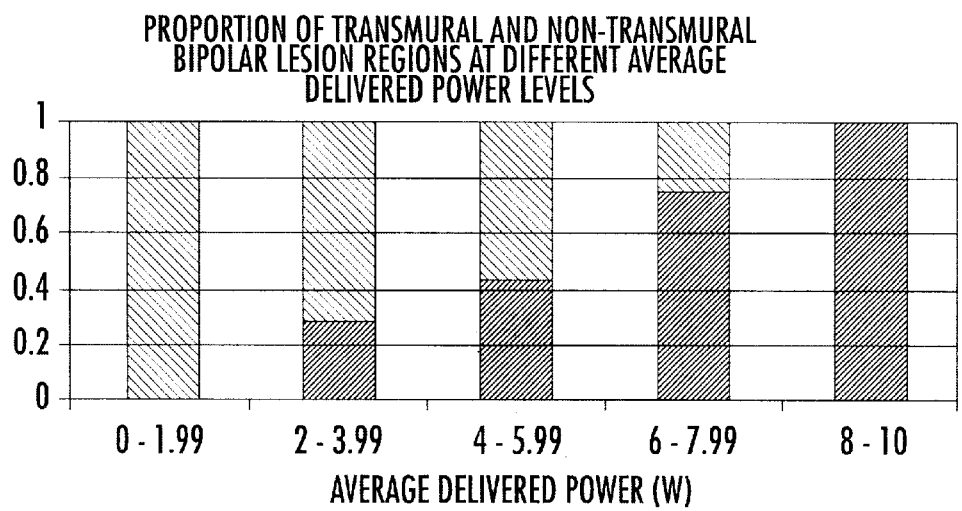
FIG. 13B is a graph of the proportion of transmural and non-transmural bipolar lesion regions at different average delivered power levels according to embodiments of the present invention.
Figure 14A:
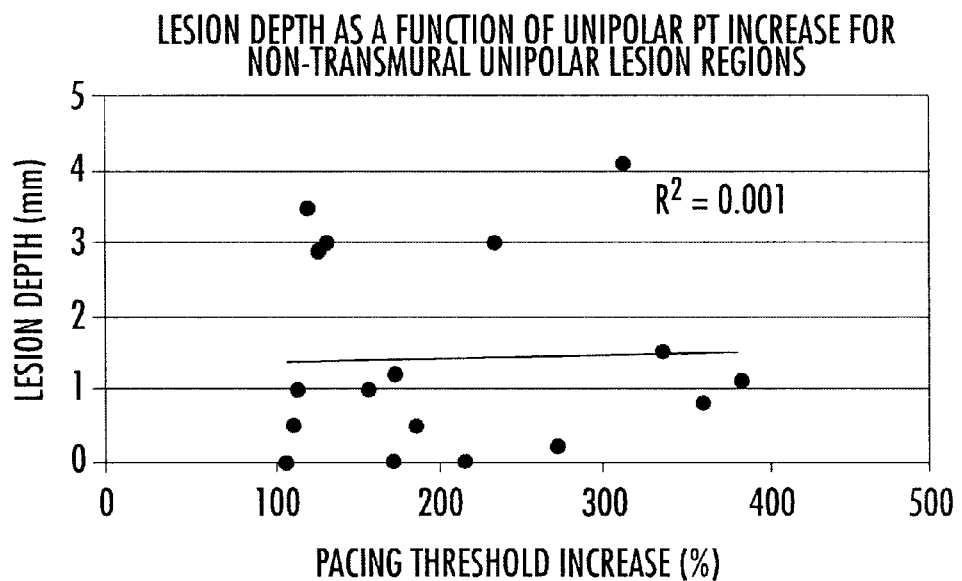
FIG. 14A is a graph of lesion depth as a function of unipolar pacing threshold increase for non-transmural unipolar lesion regions according to embodiments of the present invention.
Figure 14B:
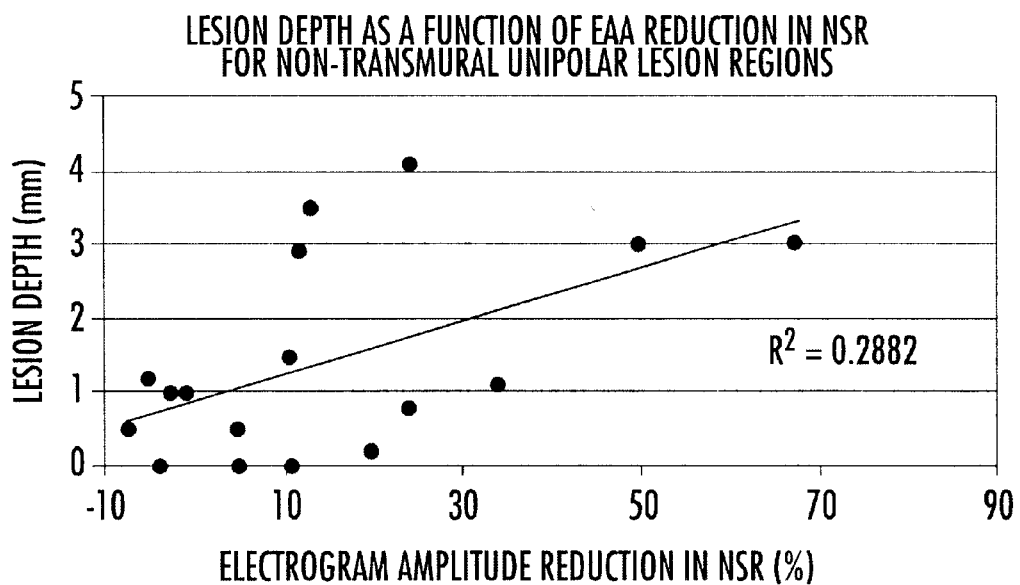
FIG. 14B is a graph of lesion depth as a function of EAA reduction in NSR for non-transmural unipolar lesion regions according to embodiments of the present invention.
Figure 15A:
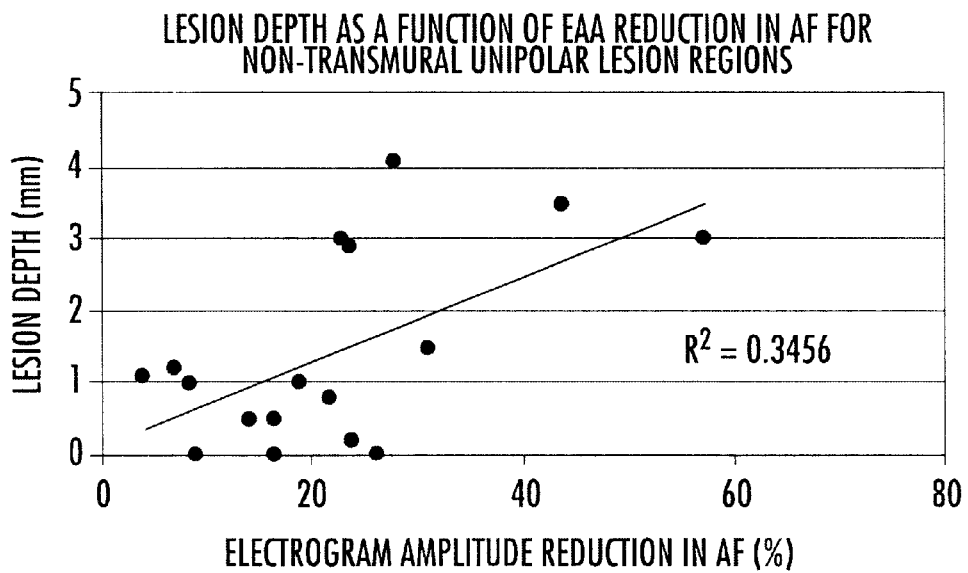
FIG. 15A is a graph of lesion depth as a function of EAA reduction in AF for non-transmural unipolar lesion regions according to embodiments of the present invention.
Figure 15B:
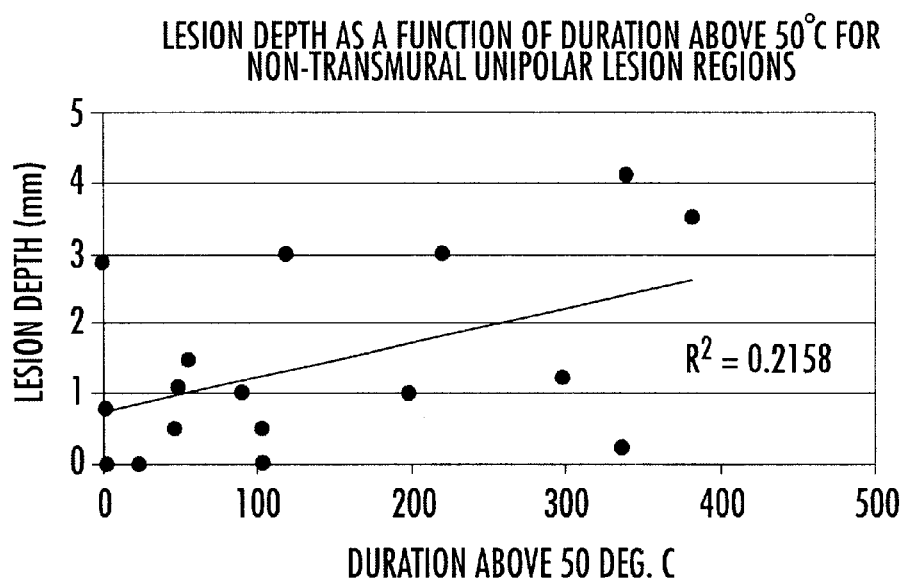
FIG. 15B is a graph of lesion depth as a function of the duration of the thermal ablation at temperatures above 50° C. for non-transmural unipolar lesion regions according to embodiments of the present invention.

FIGS. 13A and 13B show the proportion of lesion region sites that underwent different power levels, histogram style, but normalized to the total number of power levels delivered in each power level band. FIG. 13A illustrates the data for unipolar lesion regions, while FIG. 13B illustrates the data for bipolar lesion regions. The black (darker) portion of each band represents those lesion regions that were transmural, while those that are gray represent those that were not transmural.

Lesion depth as a function of different parameters: The lesion depths of the unipolar lesion regions that were not transmural were determined. These relationships are illustrated in FIGS. 14A, 14B, 15A, and 15B.

Figure 16A:
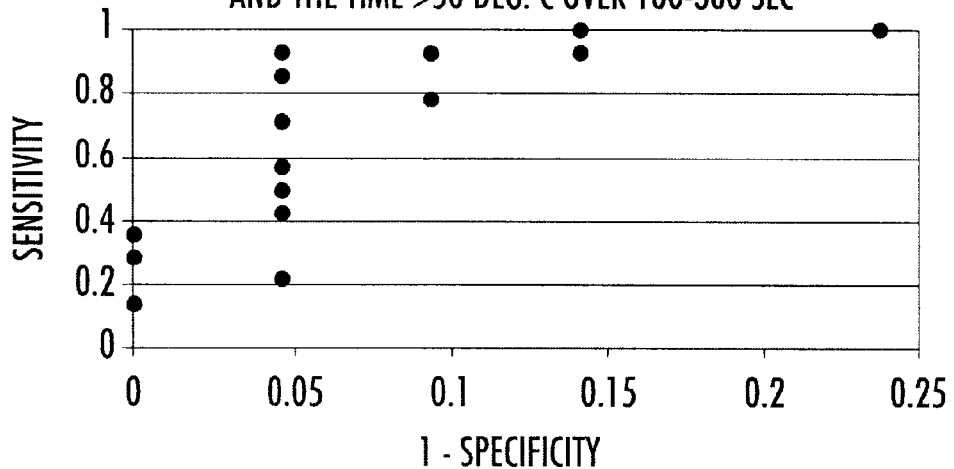
FIG. 16A is a graph of the Receiver Operating Characteristic ("ROC") curve obtained by varying the bipolar percent EAA reduction in AF over 40–60%, with an ablation time at a temperature of or over 50° C. over 180–360 seconds according to embodiments of the present invention.
Figure 16B:
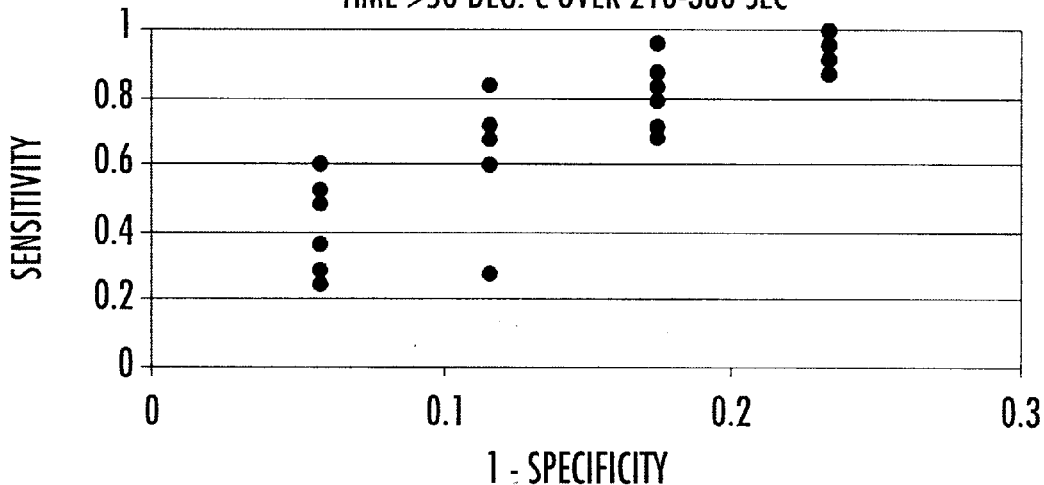
FIG. 16B is a graph of the ROC curve obtained by varying the unipolar percent EAA reduction in AF over 15–35%, with an ablation time at a temperature of about 50° C. over 210–360 seconds according to embodiments of the present invention.

Retrospective algorithm development for the prediction of lesion region transmurality: From the above data, one may develop combinations of criteria cut-offs that would allow one to retrospectively assess the sensitivity and specificity for discriminating lesion regions that are transmural vs. non-transmural. For example, using a bipolar EAA reduction in AF criterion of >45% and an ablation electrode duration >50° C. criterion of at least 240 seconds, one finds a sensitivity for detecting transmural lesion regions of 93% (13/14) and a specificity of 95% (20/21). The ROC curve shown in FIG. 16A shows the sensitivity vs. (1—specificity) for the detection of transmural lesion regions when varying these cut-off criterion of a bipolar %EAA reduction in AF over 40, 45, 50, 55, and 60%, and the duration >50° C. criterion over 180, 210, 240, 270, 300, 330, and 360 seconds. The graph shown in FIG. 16B shows the sensitivity vs. (1—specificity) for the detection of transmural lesion regions when varying these cut-off criterion of a unipolar %EAA reduction in AF over 15, 20, 25, 30, and 35%, and the duration >50° C. criterion over 180, 210, 240, 270, 300, 330, and 360 seconds. Notice the abscissa scale range is (0, 0.30).

Discussion

The primary results of this study are that the pacing thresholds and electrogram (activation) amplitudes from a multi-pole linear ablation catheter are significantly increased and decreased, respectively, after the creation of an ablation lesion, and that these changes are accentuated from electrodes adjacent to transmural regions of the lesion. Further, ablation electrodes adjacent to regions of the lesion that are transmural are maintained at lethal temperatures during longer RF energy application than those electrodes adjacent to regions of the lesion that are not transmural. Lastly, the average power delivered to the ablation electrodes were somewhat different between electrodes adjacent to transmural and nontransmural lesion regions, but not as different as the other measures investigated (pacing thresholds, electrogram signals (activation amplitudes), and duration above certain temperatures).

From the data, the sensitivity and specificity of detecting transmural lesion regions may be determined for different combinations of criteria measure cut-offs. For example, using bipolar EAA %reduction in AF of >45% and an ablation electrode duration >50° C. of at least 240 seconds, the sensitivity and specificity for detecting transmural lesion regions was found to be 93% (13/14) and 95% (20/21), respectively.

Conclusion

These data support the recognition by the inventors that electrophysiologic changes that arise due to the creation of an ablation lesion (catheter electrode pacing threshold increases and electrogram amplitude decreases) and the thermal profile of the ablation electrodes during RF energy delivery may be used to more reliably assess the transmurality of the lesion. Each or a combination of these changes may be evaluated to determine useful endpoints (delivery endpoints) in the creation of clinically efficacious linear ablation lesions (and to identify that such a lesion will be able to block myocardial propagation).

In summary, the acute sheep model of sustained AF was performed with a 6-pole ablation catheter from GUIDANT Corporation located in St. Paul, Minn., and associated phased RF ablation system. The experiment was able to correlate electrophysiologic and thermal measures acquired along the catheter during an intercaval (SVC-IVC) linear lesion procedure to regions along the lesion as being transmural or non-transmural. The electrophysiologic measures investigated were the %change in post- vs. pre-ablation 1) increase in pacing threshold (PT) in NSR, 2) decrease in electrogram amplitude in NSR, and 3) decrease in electrogram amplitude in AF. The thermal measures investigated were the duration that the catheter electrodes were maintained above certain temperatures (e.g. >50° C.) during the ablation.

The sensitivity and specificity of generating and detecting transmural lesion regions during ablation therapy sessions may be determined by employing different combinations of criteria for selected parameters including one or more of electrophysiologic, thermal, and power measures. For example, using bipolar EAA %reduction in AF of >45% and an ablation electrode duration >50° C. of at least 240 seconds, the sensitivity and specificity for detecting transmural lesion regions was found to be 93% (13/14) and 95% (20/21), respectively.

Other monitored parameters and EAA reduction values may also be employed, such as average delivered power (such as about or greater than 8W). Higher ablation exposure temperatures (with perhaps shorter times) as well as lower (i.e., 45–47 degrees C.) for longer times such as above 300 seconds total elapsed time with % EAA reduction in selected EAA signals may be used for NSR tissue. In AF, an ablation temperature of about 60° C. or greater with a treatment time of about 100–200 seconds and AF reduction in bipolar EAA of >than about 45% may also be used.

In addition, detecting EAA signals or other electrical activity signals from a plurality of electrode configurations about the lesion site over greater spatial perspectives during the ablation therapy (scanning a plurality of times intermittently or at desired intervals during the treatment time) can provide more information about the condition of the lesion (lesion depth and transmissivity) and help control the amount of thermal exposure the tissue is exposed to so that it is correlated to the formation of clinically efficacious lesions in the tissue.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for controlling the administration of an ablation treatment to cardiac tissue of a patient experiencing atrial fibrillation, comprising:
    ablating the targeted ablation treatment region to form a lesion in the cardiac tissue;
    measuring at least one electrophysiologic parameter of cardiac tissue proximate the targeted ablation treatment region after said ablating step has been commenced while the patient is in atrial fibrillation; and
    automatically determining whether the lesion formed by said ablating step is clinically efficacious.

2. A method for controlling the administration of an ablation treatment to cardiac tissue of a patient experiencing atrial fibrillation comprising:
    ablating the targeted ablation treatment region to form a lesion in the cardiac tissue;
    measuring at least one electrophysiologic parameter of cardiac tissue proximate the targeted ablation treatment region after said ablating step has been commenced while the patient is in atrial fibrillation;
    determining whether the lesion formed by said ablating step is clinically efficacious;
    measuring the at least one electrophysiologic parameter of cardiac tissue proximate a targeted ablation treatment region while the patient is in atrial fibrillation before said ablating step; and
    comparing the at least one electrophysiologic parameter obtained during said measuring steps to determine whether the lesion formed by said ablating step is clinically efficacious.

3. A method according to claim 2, wherein the at least one electrophysiologic parameter of cardiac tissue comprises the standard deviation measure of the electrogram signal.

4. A method according to claim 2, wherein said determining step further comprises considering at least one of (a) the ablation temperature and tissue exposure time, (b) the impedance of the ablated tissue, and (c) the power delivered to the ablated tissue, to assess whether the lesion is clinically efficacious.

5. A method according to claim 4, wherein said determining step comprises comparing the measured times and temperatures to a reference standard for the tissue being ablated and the ablation source.

6. A method according to claim 5, wherein said determining step considers the power delivered to the lesion site so as to identify when the lesion is transmural.

7. A method according to claim 2, wherein said measuring steps comprise obtaining a plurality of readings associated with the at least one electrophysiologic parameter from a plurality of different positions along the lesion site to assess the nature of the lesion thereat.

8. A method according to claim 2, wherein said ablating step is carried out by inserting a multi-electrode catheter into a lumen of the heart and delivering RF energy to the targeted tissue via the multiple electrodes.

9. A method according to claim 8, wherein said measuring steps comprise sensing from a plurality of different electrode configurations defined by different electrical couplings to assess the electrical activity of the lesion.

10. A method for controlling the administration of an ablation treatment to cardiac tissue of a patient experiencing atrial fibrillation comprising:
    ablating the targeted ablation treatment region to form a lesion in the cardiac tissue;
    measuring at least one electrophysiologic parameter of cardiac tissue proximate the targeted ablation treatment region after said ablating step has been commenced while the patient is in atrial fibrillation;
    determining whether the lesion formed by said ablating step is clinically efficacious; and
    automatically terminating said ablating step when the lesion is identified as clinically efficacious.

11. A method for controlling the administration of an ablation treatment to cardiac tissue of a patient experiencing atrial fibrillation, comprising:
    ablating the targeted ablation treatment region to form a lesion in the cardiac tissue;
    measuring at least one electrophysiologic parameter of cardiac tissue proximate the targeted ablation treatment region after said ablating step has been commenced while the patient is in atrial fibrillation; and
    determining whether the lesion formed by said ablating step is clinically efficacious;

wherein said ablating step is carried out using an RE ablation source which is configured to expose the targeted tissue to at least about 50° for at least about 240 seconds.

12. A method for controlling the delivery of a selected ablation treatment to cardiac tissue, comprising:

delivering a desired ablation therapy to the selected ablation treatment region to form a lesion in cardiac tissue;

obtaining first and second measurements of at least one electrophysiologic signal associated with cardiac tissue in the selected ablation treatment region proximate the lesion from a plurality of different positions associated with the lesion, wherein the first measurements are obtained before said delivering step is initiated; and identifying when sufficient tissue has been destroyed at the lesion so as to automatically stop the ablation of the tissue of said delivering step based on the first and second measurements of said obtaining step.

13. A method according to claim 12, wherein said delivering step is carried out by a multiple electrode RF ablation catheter, and wherein said obtaining step comprises sensing the electrical activity of the at least one electrophysiologic signal from a plurality of different electrical couplings of the multiple electrodes on the ablation catheter.

14. A method according to claim 13, wherein said delivering step is carried out so that the RF ablation catheter exposes the targeted tissue to at least about 50° C. for at least about 240 seconds to form the lesion.

15. A method according to claim 12, wherein said obtaining and delivering steps are carried out when the patient is in atrial fibrillation.

16. A method according to claim 15, wherein said at least one electrophysiologic signal comprises a measure of the amplitude of the local electrogram signal.

17. A method according to claim 12, wherein said obtaining and delivering steps are carried out when the patient is in intermittent fibrillation.

18. A method according to claim 12, wherein said obtaining and delivering steps are carried out when the patient is in normal sinus rhythm.

19. A method according to claim 12, wherein said identifying step comprises considering the standard deviation of the amplitude measurements of the local electrogram signal of the first and second measurements of said obtaining step.

20. A method according to claim 12, further comprising the step of measuring the ablation treatment temperature and time during said delivering step.

21. A method according to claim 20, wherein said identifying step further comprises comparing the measured ablation times and temperatures to a reference standard for the tissue being ablated and the ablation source.

22. A method according to claim 12, wherein said identifying step comprises considering at least one of the impedance of the lesion site and the delivered power to the lesion site to assess whether the lesion is clinically efficacious.

23. A method according to claim 12, wherein said identifying step is performed so as to identify when the lesion is transmural.

24. A method according to claim 12, further comprising the step of automatically terminating said delivery step when the lesion is identified as clinically efficacious based on said identifying step.

25. A method for identifying when a lesion is clinically efficacious during delivery of a selected ablation therapy to form same, comprising the steps of:

(a) measuring the standard deviation of the local electrogram signal of heart tissue proximate a targeted ablation treatment region while the patient is in atrial fibrillation;

(b) ablating the targeted ablation treatment region to form a lesion in the heart tissue;

(c) measuring the standard deviation of the local electrogram signal of heart tissue proximate the targeted ablation treatment region after said first measuring step and after said ablating step has been commenced while the patient is in atrial fibrillation; and (d) comparing the standard deviation measure of the amplitude of the local electrogram signals measured during steps (a) and (c) to determine whether the lesion formed by said ablating step is clinically efficacious.

26. A method according to claim 25, further comprising the step of measuring the impedance in the cardiac tissue about the lesion site and the power delivered to the lesion site by said ablating step.

27. A method according to claim 26, further comprising the step of considering the ablation temperature and the exposure time of the lesion to assess whether the lesion is clinically efficacious.

28. A system for ablating cardiac tissue, comprising:

an ablation source configured to expose targeted cardiac tissue to ablation sufficient to form a lesion in cardiac tissue;

a controller operably associated with the ablation source;

a power source operably associated with the controller and the ablation source; and a plurality of electrodes operably associated with the controller and configured to be positioned, in operation, proximate the lesion site of the targeted cardiac tissue to form the lesion into the cardiac tissue and sense electrical activity of the cardiac tissue;

wherein, in operation, the controller is configured to receive electrical signals corresponding to electrical activity of the cardiac tissue about the lesion from the electrodes before initiation of the thermal ablation therapy and at desired times during the ablation therapy treatment session, and analyze the electrical signals to control the duration of the ablation treatment from the ablation source, and wherein the electrodes are configured to relay information to the controller about the electrical activity of the cardiac tissue at different positions associated with the lesion and to ablate the tissue at the lesion site.

29. A system according to claim 28, wherein the ablation source comprises a multiple electrode catheter configured to transmit RF energy to the cardiac tissue.

30. A system according to claim 28, wherein the multiple electrodes are configured, in operation, to be electrically coupled in a plurality of different electrical coupling combinations to sense and relay information about the electrical activity of the lesion site to the controller.

31. A system according to claim 28, further comprising a temperature sensor positioned proximate the lesion and operably associated with the controller, wherein the controller is configured to monitor the time at which the cardiac tissue is exposed to ablation temperatures.

32. A system according to claim 28, wherein the controller is configured to monitor the electrical signals and automatically terminate the ablation therapy when the comparison of the values of the received electrical signals corresponding to electrical activity of the cardiac tissue of the lesion site to indicate that the lesion is transmural.

33. A system for ablating cardiac tissue, comprising:

an ablation source configured, in position, to expose the targeted cardiac tissue to temperatures above about 45° C. for a period of time to form a lesion in cardiac tissue;

a controller operably associated with the ablation source;

a power source operably associated with the controller and the ablation source; and at least one sensing electrode operably associated with the controller and configured, in operation, to be positioned proximate the lesion site of the targeted cardiac tissue;

wherein the controller is configured to receive electrical signals from the at least one sensing electrode before initiation of the thermal ablation therapy and at desired times during the ablation therapy treatment session when the subject is experiencing atrial fibrillation, wherein the electrical signals correspond to the measure of the standard deviation of the electrogram amplitude of the tissue during fibrillation, and wherein the controller is configured to analyze the standard deviation of the amplitude of the fibrillating tissue about the lesion to control the duration of the ablation treatment from the ablation source.

34. A system according to claim 33, wherein the at least one sensing electrode is configured to relay information about the electrical activity of the cardiac tissue associated with the lesion to the controller.

35. A system according to claim 33, wherein the ablation source comprises a multiple electrode catheter configured to transmit RF energy to the selected cardiac tissue.

36. A system according to claim 35, wherein the multiple electrodes are configured to be electrically coupled in a plurality of different electrical configurations to sense and relay information about the electrical activity about the lesion to the controller.

37. A system according to claim 36, further comprising a temperature sensor positioned proximate the lesion and operably associated with the controller, wherein the controller is configured to monitor the time at which the cardiac tissue is exposed to ablation temperatures.

38. A system according to claim 33, wherein the controller is configured to monitor the measure of the standard deviation of the electrical signals and automatically terminate the ablation therapy about the lesion when the difference between the standard deviation measures pre- and post-ablation indicate that the lesion is transmural.

39. A computer program product for identifying whether an ablation lesion in cardiac tissue of a subject being treated for a cardiac condition is clinically efficacious during an ablation therapy session, the computer program product comprising:

a computer readable storage medium having computer readable program code embodied in said medium, said computer-readable program code comprising:

computer readable program code for identifying a first measurement of the electrical activity corresponding to the standard deviation of the amplitude of the electrogram in the cardiac tissue located about a lesion site while a subject is experiencing atrial fibrillation;

computer readable program code for identifying a second measurement of the electrical activity corresponding to the standard deviation of the amplitude of the electrogram in the cardiac tissue located about the lesion site after the lesion site has been exposed to at least a portion of a selected ablation therapy; and computer readable program code for comparing the first and second measurements of the standard deviation of the amplitude of the electrogram activity to determine whether the lesion is clinically efficacious.

40. A computer program product according to claim 39, wherein said computer program product further comprises computer readable program code for assessing the amount of time, the ablation temperature, and the type of ablation therapy which the tissue proximate the lesion has been exposed and wherein the computer code for comparing the first and second measurements further considers at least one of the ablation time, temperature, type, and the delivered power during the ablation therapy and the impedance of the lesion tissue.

41. A computer program product for identifying whether an ablation lesion in cardiac tissue of a subject being treated for a cardiac condition is clinically efficacious during an ablation therapy session, the computer program product comprising:

a computer readable storage medium having computer readable program code embodied in said medium, said computer-readable program code comprising:

computer readable program code for receiving data corresponding to a first set of information regarding the electrical activity in the cardiac tissue from multiple regions about a lesion site prior to active initiation of the ablation therapy;

computer readable program code for receiving data corresponding to a second set of information regarding the electrical activity in the cardiac tissue from multiple regions about the lesion site after the lesion site has been exposed to at least a portion of a selected ablation therapy; and computer readable program code for comparing the data from the first and second sets of information to determine whether the lesion is clinically efficacious about its perimeter.

42. A computer program product according to claim 41, wherein said computer program product further comprises computer readable program code for assessing the amount of time, the ablation temperature, and the type of ablation therapy which the tissue about the lesion site has been exposed, and wherein the computer code for comparing the first and second data sets further considers at least one of (a) the ablation time, temperature, and type, or (b) the impedance of the tissue at the lesion site or the delivered power to the lesion site during the ablation therapy.

43. A computer program product according to claim 41, wherein said computer program product further comprises computer readable program code for scanning the lesion site to obtain a plurality of data sets over different sites about the lesion site during the ablation therapy.

44. A computer program product according to claim 41, wherein said computer program product further comprises computer readable program code for electrically changing couplings of electrodes used to deliver the ablation therapy to electrically sense and relay information about the electrical activity of the lesion site from a plurality of different electrode coupling perspectives during the ablation therapy session.

* * * * *

UNITED STATES PATENT AND TRADEMARK OFFICE
CERTIFICATE OF CORRECTION

PATENT NO. : 6,743,225 B2
DATED : June 1, 2004
INVENTOR(S) : Sanchez et al.

It is certified that error appears in the above-identified patent and that said Letters Patent is hereby corrected as shown below:

Column 23,
Lines 1-3, should read -- wherein said ablating step is carried out using an RF ablation source which is configured to expose the targeted tissue to at least about 50ºC for at least about --

Signed and Sealed this

Ninth Day of November, 2004

JON W. DUDAS
*Director of the United States Patent and Trademark Office*